US012157749B2

(12) United States Patent
He et al.

(10) Patent No.: US 12,157,749 B2
(45) Date of Patent: *Dec. 3, 2024

(54) BORATE-BASED DRUG AND USE THEREOF

(71) Applicant: Chengdu Origin Biotechnology Limited Company, Sichuan (CN)

(72) Inventors: Peng He, Sichuan (CN); Haiyan Li, Sichuan (CN); Hai Zhao, Sichuan (CN); Pei Huang, Sichuan (CN); Xuechao Wang, Sichuan (CN)

(73) Assignee: Chengdu Origin Biotechnology Limited Company (CN)

( * ) Notice: Subject to any disclaimer, the term of this patent is extended or adjusted under 35 U.S.C. 154(b) by 809 days.

This patent is subject to a terminal disclaimer.

(21) Appl. No.: 17/273,964

(22) PCT Filed: Sep. 5, 2019

(86) PCT No.: PCT/CN2019/104487
§ 371 (c)(1),
(2) Date: Mar. 5, 2021

(87) PCT Pub. No.: WO2020/052488
PCT Pub. Date: Mar. 19, 2020

(65) Prior Publication Data
US 2021/0332069 A1    Oct. 28, 2021

(30) Foreign Application Priority Data
Sep. 14, 2018 (CN) .......................... 201811074536.2

(51) Int. Cl.
*C07F 5/02* (2006.01)
*A61K 45/06* (2006.01)
*A61P 35/02* (2006.01)

(52) U.S. Cl.
CPC .............. *C07F 5/025* (2013.01); *A61K 45/06* (2013.01); *A61P 35/02* (2018.01)

(58) Field of Classification Search
CPC .................................. C07F 5/025; A61P 35/02
See application file for complete search history.

(56) References Cited

U.S. PATENT DOCUMENTS 7,442,830 B1    10/2008   Olhava et al.
8,859,504 B2 *  10/2014   Elliott ..................... A61P 37/06
(Continued)

FOREIGN PATENT DOCUMENTS

| CN | 101772507 A | 7/2010 |
| CN | 103435638 A | 12/2013 |

(Continued)

OTHER PUBLICATIONS

Tong et al. J. Serb. Chem. Soc. 82 (9) 1025-1037 (2017) UDC 546.273-325+547.466.1:66.097.8:539.16 JSCS-5020 doi:10.2298/jsc161227047t (Year: 2017).*

(Continued)

*Primary Examiner* — Jeffrey S Lundgren
*Assistant Examiner* — Anthony Joseph Seitz
(74) *Attorney, Agent, or Firm* — Lerner David LLP

(57) ABSTRACT

The present application provides a borate ester compound suitable for being used as a proteasome inhibitor, a preparation method and use thereof, and the compound has the following structure formula (I)

(Continued)

wherein, $R_1$, $R_2$ is asymmetric substituent in para-position, and $R_1$ and $R_2$ are both selected from the group consisting of halogen; and when $R_1$ is F, $R_2$ is not Cl; when $R_1$ is Cl, $R_2$ is not Br or F; and when $R_1$ is Br, $R_2$ is not Cl; $X_1$, $X_2$ is selected from the group consisting of hydroxyl, or $X_1$ and $X_2$ together form a substituted or unsubstituted 4 to 10 membered ring containing 1 to 4 heteroatoms being selected from the group consisting of O, N and S.

10 Claims, 2 Drawing Sheets

(56) References Cited

U.S. PATENT DOCUMENTS

| | | | | |
|---|---|---|---|---|
| 9,175,017 | B1 * | 11/2015 | Elliott | C07K 5/06191 |
| 9,175,018 | B2 * | 11/2015 | Elliott | A61P 17/02 |
| 10,526,351 | B2 * | 1/2020 | Elliott | A61K 31/69 |
| 10,604,538 | B2 * | 3/2020 | Elliott | A61P 43/00 |
| 11,414,437 | B2 * | 8/2022 | He | A61P 35/00 |
| 11,485,746 | B2 * | 11/2022 | Elliott | C07F 5/025 |
| 2009/0042836 | A1 | 2/2009 | Olhava et al. | |
| 2009/0325903 | A1 | 12/2009 | Elliott et al. | |
| 2010/0204180 | A1 | 8/2010 | Olhava et al. | |
| 2013/0096068 | A1 | 4/2013 | Sheshbaradaran | |
| 2013/0165390 | A1 | 6/2013 | Elliott et al. | |
| 2013/0331595 | A1 | 12/2013 | Olhava et al. | |
| 2014/0343314 | A1 * | 11/2014 | Elliott | A61P 35/04 |
| 2018/0235986 | A1 | 8/2018 | Labotka et al. | |
| 2020/0165272 | A1 | 5/2020 | He et al. | |

FOREIGN PATENT DOCUMENTS

| | | |
|---|---|---|
| CN | 106496259 A | 3/2017 |
| CN | 107400142 A | 11/2017 |
| CN | 108440583 A | 8/2018 |
| CN | 109305980 A | 2/2019 |
| CN | 110041353 A | 7/2019 |
| EP | 2527347 A1 | 11/2012 |
| EP | 2730579 A1 | 5/2014 |
| EP | 2730580 A1 | 5/2014 |
| JP | 2010535759 A | 11/2010 |
| JP | 2011524903 A | 9/2011 |
| JP | 2018506550 A | 3/2018 |
| WO | 2009020448 A1 | 2/2009 |
| WO | 2009154737 A1 | 12/2009 |
| WO | 2016133903 A2 | 8/2016 |
| WO | 2017198194 A1 | 11/2017 |

OTHER PUBLICATIONS

International Search Report for Application No. PCT/CN2019/104487 dated Dec. 4, 2019.
Extented European Search Report for Application No. 19860839.0 dated May 3, 2022. 7 pgs.

* cited by examiner

BORATE-BASED DRUG AND USE THEREOF

CROSS-REFERENCE TO RELATED APPLICATIONS

The present application is a national phase entry under 35 U.S.C. § 371 of International Application No. PCT/CN2019/104487, filed Sep. 5, 2019, which claims priority from Chinese Patent Application No. 201811074536.2 filed Sep. 14, 2018, all of which are incorporated herein by reference.

TECHNICAL FIELD

The application relates to the field of medicinal chemistry. In particular, it relates to borate esters anti-tumor drugs as proteasome inhibitor.

BACKGROUND

Boric acid and borate esters compounds show a variety of medical and pharmaceutical biological activities due to their unique structural characteristics. Proteasome is an important part of ubiquitin-proteasome system, which is responsible for the regulation and degradation of most intracellular proteins and plays a central role in regulating cell cycle, cell proliferation and apoptosis. Bortezomib (trade name: Velcade®), a boric acids drug, is the first targeting proteasome inhibitor approved by FDA in 2003. It is a new anti-tumor drug developed by Millennium Pharmaceutical Company in the United States, which is freeze-dried powder for injection and used for the treatment of refractory or recurrent multiple myeloma. Bortezomib can selectively bind with threonine at the active site of proteasome, degrade and change the level of regulatory protein in vivo, destroy cell stability, and lead to the death of tumor cells.

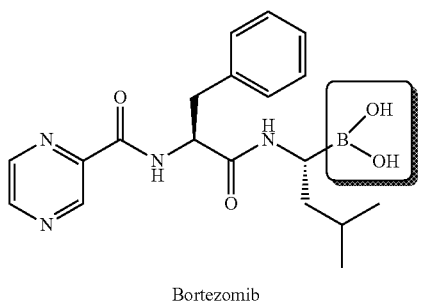

Bortezomib

Ixazomib Citrate(MLN9708, trade name: Ninlaro®), the second generation proteasome inhibitor developed by Millennium pharmaceutical company based on Bortezomib, was approved by FDA in the United States on Nov. 20, 2015 for the treatment of multiple myeloma (MM). It can preferentially bind with and inhibit chymotrypsin-like proteolysis (O5) site of 20S proteasome, and inhibit the proliferation of idiopathic myeloma cells by blocking protease. As a prodrug, borate ester compound MLN9708 is rapidly hydrolyzed into active MLN2238 having boric acid structure in vivo to exert pharmacological activity. Since the unstable boric acid group is converted into a stable borate ester structure, the biggest advantage of MLN9708 over MLN2238 and Bortezomib is that the injection dosage form can be changed to the oral capsule dosage form, which greatly improves the patient's drug compliance.

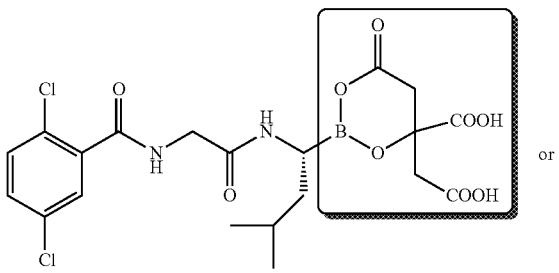 or

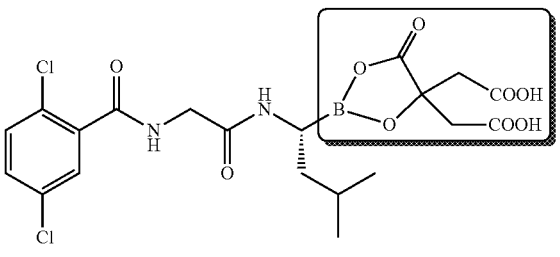

MLN9708 (Ixazomib Citrate)

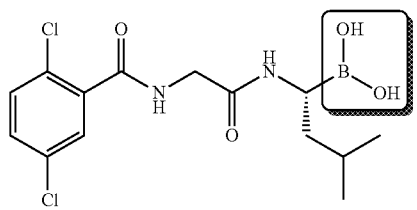

MLN2238 (Ixazomib)

In addition, patent document CN103435638A discloses a compound (81) with the following structure in an Example.

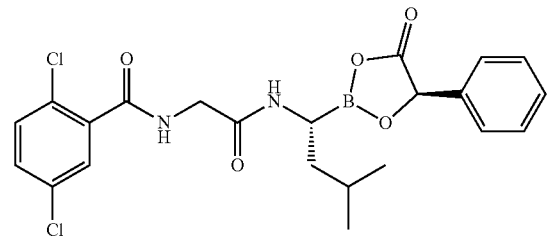

81

In the prior art, there is still a need to develop borate ester compounds with higher anticancer activities.

SUMMARY OF THE INVENTION

In order to solve the above technical problems, one or more embodiments of the present application provide a borate ester compound of the following formula (I) or pharmaceutically acceptable salts, solvates, complexes or boric anhydrides thereof.

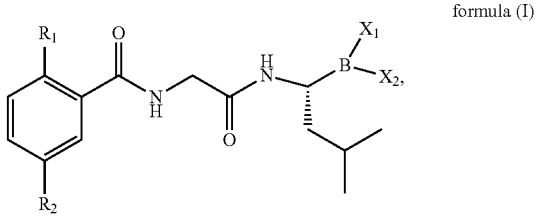

formula (I)

wherein, $R_1$, $R_2$ is asymmetric substituent in para-position, and $R_1$ and $R_2$ are both selected from the group consisting of halogen; and when $R_1$ is F, $R_2$ is not Cl; when $R_1$ is Cl, $R_2$ is not Br or F; and when $R_1$ is Br, $R_2$ is not Cl;

$X_1$, $X_2$ is selected from the group consisting of hydroxyl, or $X_1$ and $X_2$ together form a substituted or unsubstituted 4 to 10 membered ring containing 1 to 4 heteroatoms being selected from the group consisting of O, N and S.

In one or more embodiments of the present application, $X_1$ and $X_2$ together with the boron atom form a substituted or unsubstituted 5 to 6 membered ring containing 1 to 2 O atoms or 1 to 2 N atoms.

In one or more embodiments of the present application, the structure of the 5 to 6 membered ring formed by $X_1$ and $X_2$ together with boron atom is shown as follows:

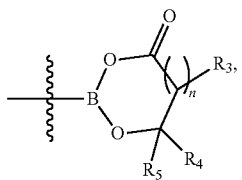

wherein, when n=1, $R_3$, $R_4$ and $R_5$ are selected from the group consisting of H, self-substituted or unsubstituted $C_1$-$C_6$ alkyl, self-substituted or unsubstituted cycloalkyl, substituted or unsubstituted $C_3$-$C_8$ alkoxy, substituted or unsubstituted $C_1$-$C_6$ alkyl-COOH, —COOH, substituted or unsubstituted benzyl, substituted or unsubstituted phenyl;

or, when n=1, $R_3$ and $R_4$ together form a saturated or unsaturated 5 to 6 membered ring being selected from the group consisting of benzene ring, cyclohexyl containing 0 to 2 unsaturated ethylenic bonds and cyclopentyl containing 0 to 2 unsaturated ethylenic bonds;

when n=0, $R_3$ does not exist, $R_4$ and $R_5$ are selected from the group consisting of H, substituted or unsubstituted $C_1$-$C_6$ alkyl, self-substituted or unsubstituted cycloalkyl, substituted or unsubstituted $C_3$-$C_8$ alkoxy, substituted or unsubstituted $C_1$-$C_6$ alkyl-COOH, —CH$_2$—COOH, —COOH, substituted or unsubstituted benzyl and substituted or unsubstituted phenyl.

In one or more embodiments of the present application, when $R_1$ is Br, $R_2$ is F or I; when $R_1$ is F, $R_2$ is Br or I.

In one or more embodiments of the present application, when $R_1$ is F and $R_2$ is Br, wherein
when n=1, $R_3$ is H, $R_4$ and $R_5$ are selected from the group consisting of H, —COOH, —CH$_2$—COOH, phenyl and benzyl; preferably, $R_4$ and $R_5$ are selected from the group consisting of —COOH and —CH$_2$—COOH, or $R_4$ and $R_5$ are alternatively being selected from the group consisting of phenyl and hydrogen atom; further preferably, $R_4$ and $R_5$ are alternatively being selected from the group consisting of —CH$_2$—COOH and —COOH;

or when n=1, $R_3$ and $R_4$ together form a substituted or unsubstituted 6 membered ring being selected from the group consisting of benzene ring or cyclohexyl containing 0 to 2 unsaturated ethylenic bonds, and $R_5$ does not exist; and the 6 membered ring is preferably a benzene ring;

or when n=0, $R_3$ does not exist, $R_4$ and $R_5$ are selected from the group consisting of H, —COOH, CH$_2$—COOH, phenyl and benzyl; preferably, $R_4$ and $R_5$ are selected from the group consisting of —COOH and —CH$_2$—COOH, or $R_4$ and $R_5$ are selected from the group consisting of phenyl and hydrogen atom; further preferably, $R_4$ and $R_5$ are both —CH$_2$—COOH, or $R_4$ and $R_5$ are alternatively being selected from the group consisting of phenyl and hydrogen atom, and the carbon atom on the 5 membered ring which is connected with phenyl is in S configuration.

In one or more embodiments of the present application, when n=1, the structure of the ring is

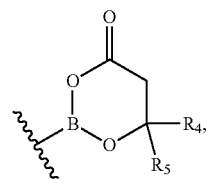

wherein $R_4$ and $R_5$ are selected from the group consisting of —COOH and —CH$_2$—COOH, or $R_4$ and $R_5$ are alternatively being selected from the group consisting of phenyl and hydrogen atom;

or n=1, $R_3$ and $R_4$ together form a 6 membered ring which has a structure of

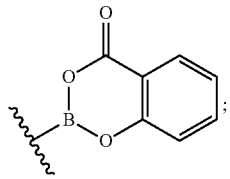 [SMILES: *B1OC(=O)c2ccccc2O1]

or n=0, the 6 membered ring has a structure of

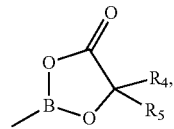

wherein, $R_4$ and $R_5$ are selected from the group consisting of —COOH and —CH$_2$—COOH, or $R_4$ and $R_5$ are selected from the group consisting of phenyl and hydrogen atom.

One or more embodiments of the present application provide a compound of formula (I') or stereoisomers, enantiomers, tautomers or mixture thereof, or pharmaceutically acceptable salts, solvates, prodrugs or boric anhydride thereof.

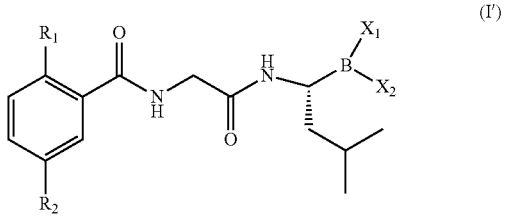

(I')

when R₁ is F, R₂ is Br; when R₁ is Br, R₂ is F;

X₁ and X₂ are OH; or

X₁ and X₂ together with the boron atom to which they are connected form a ring structure, and the ring structure is

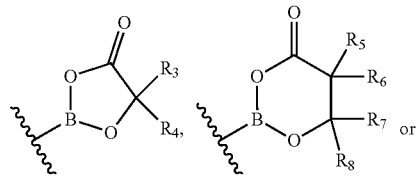

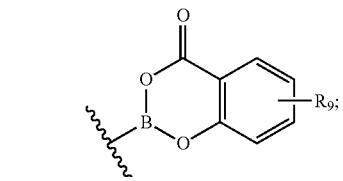

wherein

R₃, R₄, R₅, R₆, R₇, R₈ and R₉ are each independently hydrogen, $C_1$-$C_6$ alkyl, $C_1$-$C_6$ alkenyl, $C_1$-$C_6$ alkynyl, $C_1$-$C_6$ alkoxy, $C_3$-$C_8$ cycloalkyl, 3 to 7 membered heterocycloalkyl, phenyl, benzyl, 5 to 10 membered heteroaryl, COOH, $C_1$-$C_6$ alkyl-COOH, OH or halogen, wherein the $C_1$-$C_6$ alkyl, the $C_1$-$C_6$ alkenyl, the $C_1$-$C_6$ alkynyl, the $C_1$-$C_6$ alkoxy, the $C_3$-$C_8$ cycloalkyl, the 3 to 7 membered heterocycloalkyl, the phenyl, the benzyl, the 5 to 10 membered heteroaryl and the $C_1$-$C_6$ alkyl-COOH are optionally substituted with groups being selected from the group consisting of halogen, $C_1$-$C_6$ alkyl, $C_1$-$C_6$ haloalkyl, amino, cyano, acyl, carboxyl, $C_1$-$C_6$ alkyl-COOH, hydroxy, $C_1$-$C_6$ alkoxy, $C_1$-$C_6$ haloalkoxy, carbonyl, 3 to 7 membered heterocycloalkyl, $C_5$-$C_{10}$ aryl and 5 to 10 membered heteroaryl.

In some embodiments, boric acid compounds can form anhydrides by dehydrating boric acid moiety. "Boric anhydride" refers to a compound formed by combining two or more boric acid compound molecules while losing one or more water molecules. After each borate ester or boric acid complex is hydrolyzed to form a free boric acid compound, boric anhydride can also be formed. When mixed with water, boric anhydride compound is hydrolyzed to release free boric acid compound. In various embodiments, boric anhydride may contain two, three, four or more boric acid units, and may have a cyclic or linear configuration. Non-limiting embodiments of boric anhydride of the present invention include:

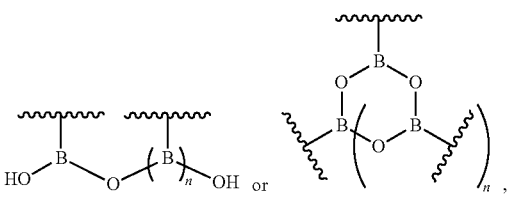

wherein n is an integer from 1 to 100.

In one or more embodiments of the present application, n is 1, 2, 3, 4, 5, 6, 7, 8, 9, 10, 20, 30, 40, 50, 60, 70, 80, 90, or 100.

In one or more embodiments of the present application, when R₁ is F, R₂ is Br,

In one or more embodiments of the present application, the ring structure is

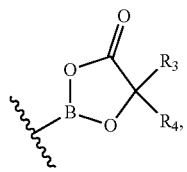

wherein,

R₃ and R₄ are each independently hydrogen, $C_1$-$C_6$ alkyl, $C_1$-$C_6$ alkoxy, $C_3$-$C_8$ cycloalkyl, 3 to 7 membered heterocycloalkyl, phenyl, benzyl, 5 to 10 membered heteroaryl, COOH or $C_1$-$C_6$ alkyl-COOH, and the $C_1$-$C_6$ alkyl, the $C_1$-$C_6$ alkoxy, the $C_3$-$C_5$ cycloalkyl, the 3 to 7 membered heterocycloalkyl, the phenyl, the benzyl, the 5 to 10 membered heteroaryl and $C_1$-$C_6$ alkyl-COOH are optionally substituted by groups being selected from the group consisting of halogen, $C_1$-$C_6$ alkyl, $C_1$-$C_6$ haloalkyl, amino, cyano, acyl, carboxyl, $C_1$-$C_6$ alkyl-COOH, hydroxy, $C_1$-$C_6$ alkoxy, $C_1$-$C_6$ haloalkoxy, carbonyl, 3 to 7 membered heterocycloalkyl, $C_5$-$C_{10}$ aryl and 5 to 10 membered heteroaryl.

In one or more embodiments of the present application, the ring structure is

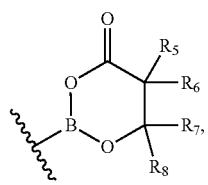

wherein,

R₅ and R₆ are each independently hydrogen, $C_1$-$C_6$ alkyl or $C_1$-$C_6$ alkoxy;

R₇ and R₈ are each independently hydrogen, $C_1$-$C_6$ alkyl, $C_1$-$C_6$ alkoxy, $C_3$-$C_8$ cycloalkyl, 3 to 7 membered heterocycloalkyl, phenyl, benzyl, 5 to 10 membered heteroaryl, COOH or $C_1$-$C_6$ alkyl-COOH;

the $C_1$-$C_6$ alkyl, the $C_1$-$C_6$ alkoxy, the $C_3$-$C_8$ cycloalkyl, the 3 to 7 membered heterocycloalkyl, the phenyl, the benzyl, the 5 to 10 membered heteroaryl and the $C_1$-$C_6$ alkyl-COOH are optionally substituted by groups being selected from the group consisting of halogen, $C_1$-$C_6$ alkyl, $C_1$-$C_6$ haloalkyl, amino, cyano, acyl, carboxyl, $C_1$-$C_6$ alkyl-COOH, hydroxy, $C_1$-$C_6$ alkoxy, $C_1$-$C_6$ haloalkoxy, carbonyl, 3 to 7 membered heterocycloalkyl, $C_5$-$C_{10}$ aryl and 5 to 10 membered heteroaryl.

In one or more embodiments of the present application, $R_5$ and $R_6$ are H, $R_7$ and $R_8$ are each independently hydrogen, $C_1$-$C_6$ alkyl, $C_1$-$C_6$ alkoxy, COOH or $C_1$-$C_6$ alkyl-COOH, and the $C_1$-$C_6$ alkyl, the $C_1$-$C_6$ alkoxy and the $C_1$-$C_6$ alkyl-COOH are optionally substituted by groups being selected from the group consisting of halogen, $C_1$-$C_6$ alkyl, $C_1$-$C_6$ haloalkyl, amino, cyano, acyl, carboxyl, $C_1$-$C_6$ alkyl-COOH, hydroxy, $C_1$-$C_6$ alkoxy, $C_1$-$C_6$ haloalkoxy, carbonyl, 3 to 7 membered heterocycloalkyl, $C_5$-$C_{10}$ aryl and 5 to 10 membered heteroaryl.

In one or more embodiments of the present application, the ring structure is

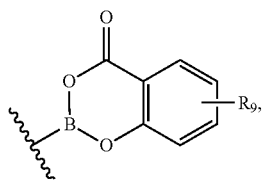

wherein, $R_9$ is hydrogen, $C_1$-$C_6$ alkyl, $C_1$-$C_6$ alkoxy, $C_3$-$C_8$ cycloalkyl, COOH or $C_1$-$C_6$ alkyl-COOH, and the $C_1$-$C_6$ alkyl, the $C_1$-$C_6$ alkoxy, the $C_3$-$C_8$ cycloalkyl and the $C_1$-$C_6$ alkyl-COOH are optionally substituted by groups being selected from the group consisting of halogen, $C_1$-$C_6$ alkyl, $C_1$-$C_6$ haloalkyl, amino, cyano, acyl, carboxyl, $C_1$-$C_6$ alkyl-COOH, hydroxy, $C_1$-$C_6$ alkoxy, $C_1$-$C_6$ haloalkoxy and carbonyl.

In one or more embodiments of the present application, wherein:

the ring structure is

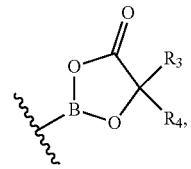

wherein $R_3$ and $R_4$ are each independently hydrogen, $C_1$-$C_6$ alkyl, phenyl, benzyl, COOH or $C_1$-$C_6$ alkyl-COOH; preferably, $R_3$ and $R_4$ are each independently hydrogen, phenyl, COOH or $C_{1\text{-}3}$ alkyl-COOH; or the ring structure is

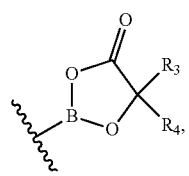

wherein $R_5$ and $R_6$ are each independently hydrogen or $C_1$-$C_6$ alkyl; and $R_7$ and $R_8$ are each independently H, COOH or $C_1$-$C_6$ alkyl-COOH; preferably, both $R_5$ and $R_6$ are H, and $R_7$ and $R_8$ are each independently COOH or $C_{1\text{-}3}$ alkyl-COOH; or the ring structure is

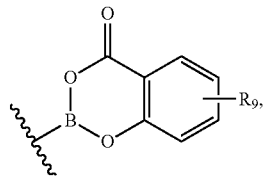

wherein $R_9$ is hydrogen, $C_1$-$C_6$ alkyl, COOH or $C_1$-$C_6$ alkyl-COOH; preferably, $R_9$ is hydrogen, $C_1$-$C_3$ alkyl, COOH or $C_1$-$C_3$ alkyl-COOH.

In one or more embodiments of the present application, wherein:

the ring structure is

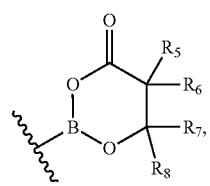

$R_3$ and $R_4$ are each independently hydrogen, phenyl, COOH or $CH_2$—COOH; or the ring structure is

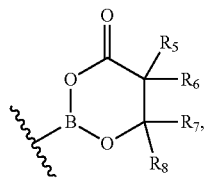

wherein $R_5$ and $R_6$ are hydrogen; $R_7$ and $R_8$ are independently COOH or $CH_2$—COOH; or the ring structure is

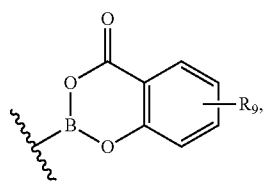

wherein $R_9$ is hydrogen.

In one or more embodiments of the present application, wherein:

when $R_1$ is F, $R_2$ is Br.
the ring structure is

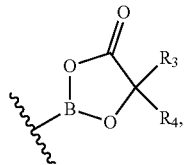

wherein $R_3$ and $R_4$ are each independently hydrogen, phenyl, COOH or CH$_2$—COOH; or
the ring structure is

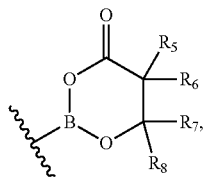

wherein $R_5$ and $R_6$ are hydrogen; $R_7$ and $R_8$ are independently hydrogen, COOH or CH$_2$—COOH; or
the ring structure is

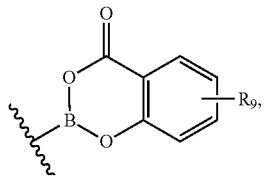

wherein $R_9$ is hydrogen.

In one or more embodiments of the present application, the compound of the present application has the following structure:

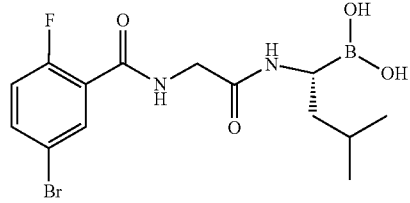
4b

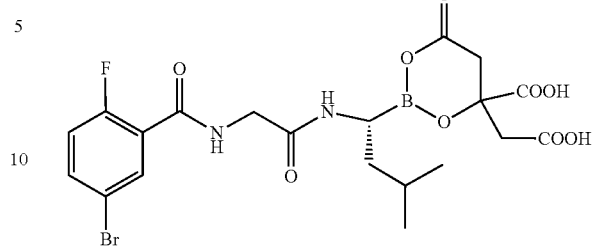
6b

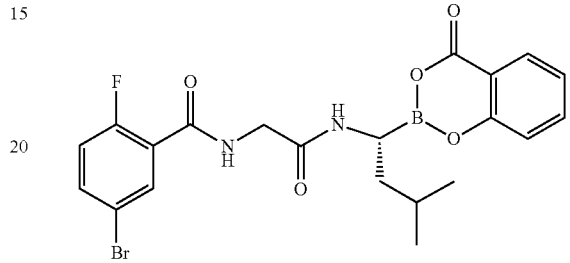
6d

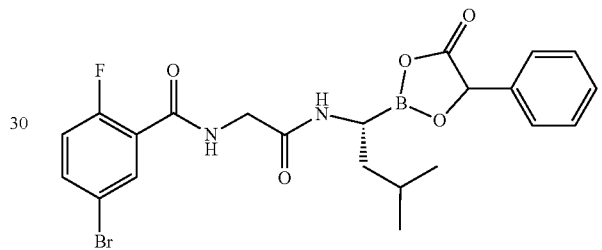
6e

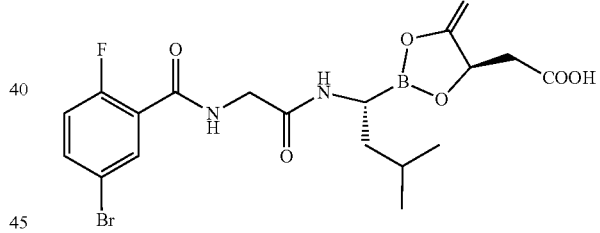
6f

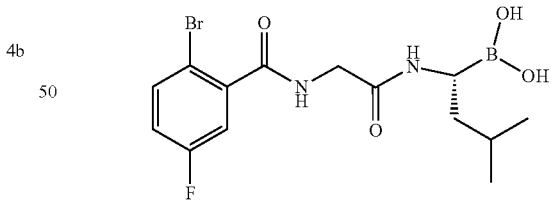
6g

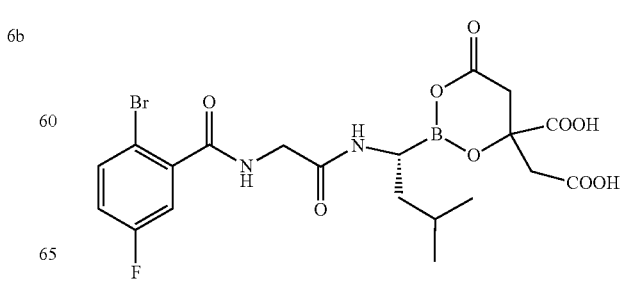
4d

6h

-continued

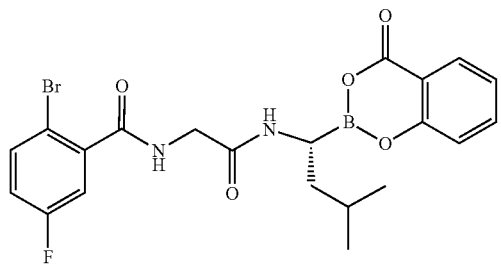
6i

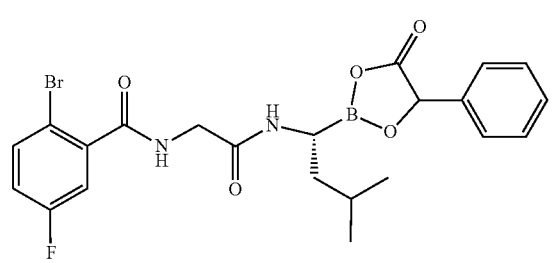
6j

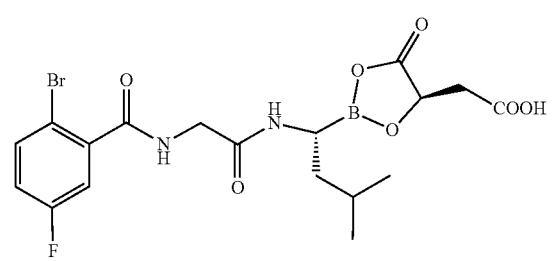
6k

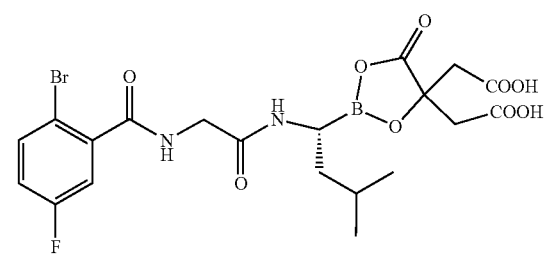
6l

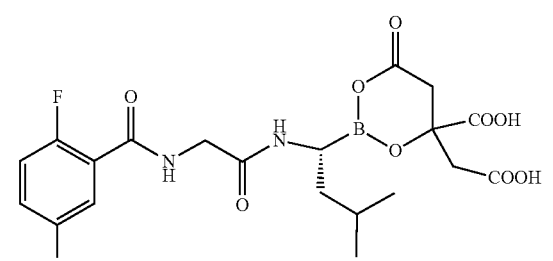
6m

-continued

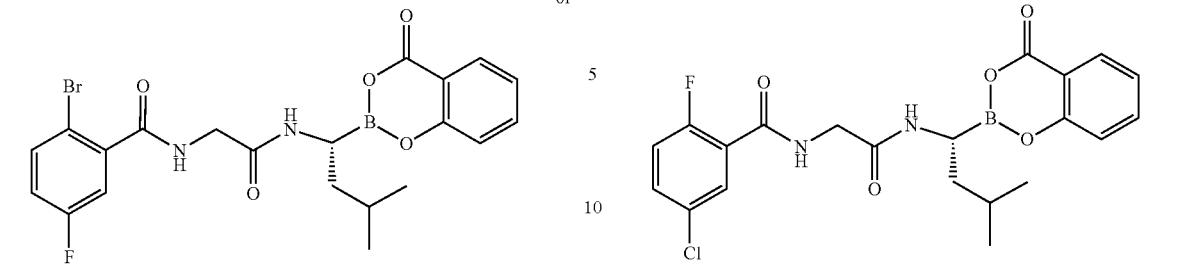
6n

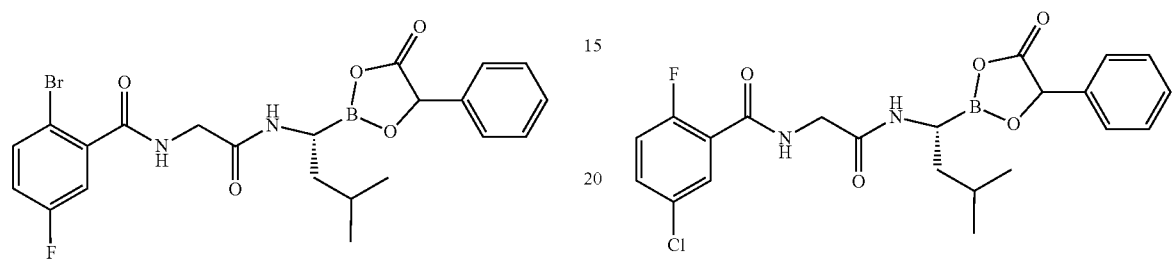
6o

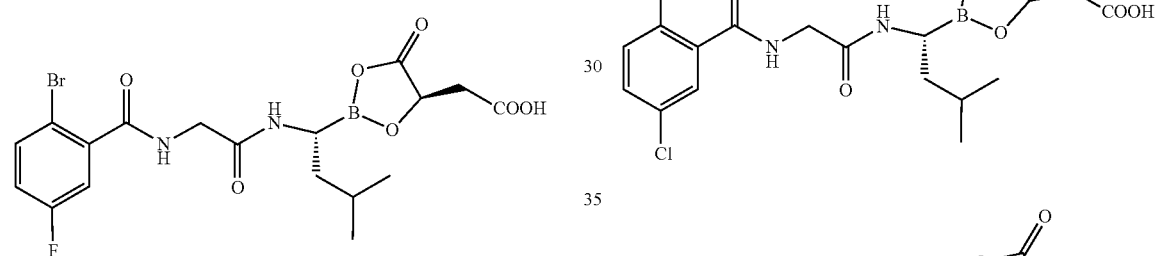
6p

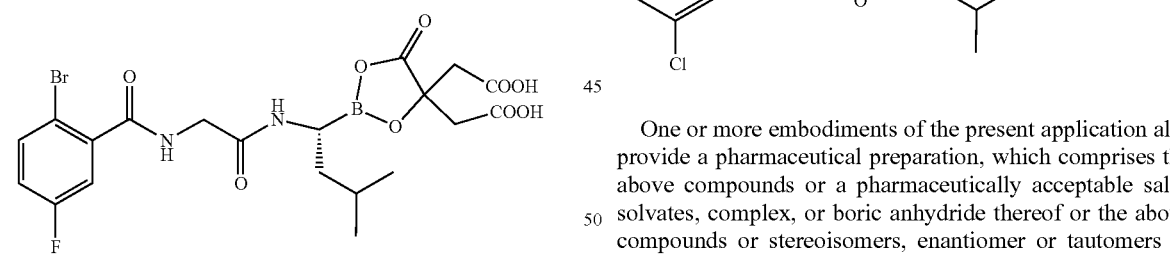
6q

One or more embodiments of the present application also provide a pharmaceutical preparation, which comprises the above compounds or a pharmaceutically acceptable salts, solvates, complex, or boric anhydride thereof or the above compounds or stereoisomers, enantiomer or tautomers or mixtures thereof, or pharmaceutically acceptable salts, solvates or prodrugs thereof, and pharmaceutically acceptable excipients.

One or more embodiments of the present application also provide a pharmaceutical composition containing the above compounds or pharmaceutically acceptable salts, solvates, complexes or boric anhydride thereof, or the above compounds, or stereoisomers, enantiomers, tautomers or mixtures thereof, or pharmaceutically acceptable salts, solvates or prodrugs thereof, and one or more other drugs for preventing and treating tumors.

One or more embodiments of the present application also provide use of the above compounds or salts, solvates, or complexes thereof, or the above compounds, or stereoisomers, enantiomers, tautomers or mixtures thereof, or pharmaceutically acceptable salts, solvates or prodrugs thereof, or the above pharmaceutical preparation or the above pharmaceutical composition in preparation of drugs for preventing and/or treating tumors.

In one or more embodiments of the present application, the drugs for treating tumor are proteasome inhibitors drugs.

In one or more embodiments of the present application, the drugs for treating tumor are proteasome inhibitor anticancer drugs, including: drugs for preventing and/or treating plasmacytoma, such as drugs for preventing and/or treating multiple myeloma; drugs for preventing and/or treating lymphoma, such as drugs for preventing and/or treating non-Hodgkin's lymphoma, mantle cell lymphoma and/or follicular lymphoma; drugs for preventing and/or treating leukemia; and drugs for preventing and treating mantle cell tumor, breast cancer, liver cancer, colon cancer, cervical cancer, lung cancer, lymphoma, ovarian cancer, renal cancer, gastric cancer, nasopharyngeal carcinoma, leukemia, melanoma, thyroid cancer, pancreatic cancer, adenocarcinoma and squamous cell carcinoma.

In one or more embodiments of the present application, the compounds of the present application can be used to treat plasmacytoma, mantle cell tumor, multiple myeloma, melanoma, breast cancer, liver cancer, cervical cancer, lung cancer, lymphoma, leukemia, ovarian cancer, renal cancer, gastric cancer, nasopharyngeal cancer, thyroid cancer, pancreatic cancer, prostate cancer, adenocarcinoma, mouth cancer, esophageal cancer, squamous cell cancer and colon cancer.

One or more embodiments of the present application also provide use of the compounds of the present application or pharmaceutically acceptable salts, solvates, complexes or boric anhydride thereof, or the compounds of the present application, or stereoisomers, enantiomers, tautomers or mixtures thereof, or pharmaceutically acceptable salts, solvates or prodrugs thereof, or the above pharmaceutical preparation or the above pharmaceutical composition in preparation of protease inhibitors.

One or more embodiments of the present application also provide use of the compounds of the present application or pharmaceutically acceptable salts, solvates, complexes or boric anhydride thereof, or the compounds of the present application, or stereoisomers, enantiomers, tautomers or mixtures thereof, or pharmaceutically acceptable salts, solvates or prodrugs thereof, or the above pharmaceutical preparation or the above pharmaceutical composition for inhibiting protease.

One or more embodiments of the present application further provide a pharmaceutical composition or a pharmaceutical preparation comprising the compounds of the present application. For example, the compounds described herein can be administered in pure form, in combination with other active ingredients, or in combination with pharmaceutically acceptable non-toxic excipients or carriers.

One or more embodiments of the present application also provide a method for preventing and/or treating cancers or tumors, comprising administering the compounds of the present application or pharmaceutically acceptable salts, solvates, complexes or boric anhydride thereof, or the compounds of the present application, or stereoisomers, enantiomers, tautomers or mixtures thereof, or pharmaceutically acceptable salts, solvates or prodrugs thereof, or the above pharmaceutical preparation or the above pharmaceutical composition to a subject in need thereof.

In one or more embodiments of the present application, the cancers or tumors are selected from the group consisting of plasmacytoma, mantle cell tumor, multiple myeloma, melanoma, breast cancer, liver cancer, cervical cancer, lung cancer, lymphoma, leukemia, ovarian cancer, renal cancer, gastric cancer, nasopharyngeal cancer, thyroid cancer, pancreatic cancer, prostate cancer, adenocarcinoma, mouth cancer, esophageal cancer, squamous cell cancer and colon cancer.

One or more embodiments of the present application also provide a method for inhibiting protease, comprising administering the compounds of the present application or pharmaceutically acceptable salts, solvates, complexes or boric anhydride thereof, or the compounds of the present application, or stereoisomers, enantiomers, tautomers or mixtures thereof, or pharmaceutically acceptable salts, solvates or prodrugs thereof, or the above pharmaceutical preparation or the above pharmaceutical composition to a subject in need thereof.

One or more embodiments of the present application also provide the compounds of the present application or pharmaceutically acceptable salts, solvates, complexes or boric anhydride thereof, or the compounds of the present application, or stereoisomers, enantiomers, tautomers or mixtures thereof, or pharmaceutically acceptable salts, solvates or prodrugs thereof, or the above pharmaceutical preparation or the above pharmaceutical composition, which are used as a drug.

One or more embodiments of the present application also provide the compounds of the present application or pharmaceutically acceptable salts, solvates, complexes or boric anhydride thereof, or the compounds of the present application, or stereoisomers, enantiomers, tautomers or mixtures thereof, or pharmaceutically acceptable salts, solvates or prodrugs thereof, or the above pharmaceutical preparation or the above pharmaceutical composition, which are used in a method for preventing and/or treating cancers or tumors.

In one or more embodiments of the present application, the cancers or tumors are selected from the group consisting of plasmacytoma, mantle cell tumor, multiple myeloma, melanoma, breast cancer, liver cancer, cervical cancer, lung cancer, lymphoma, leukemia, ovarian cancer, renal cancer, gastric cancer, nasopharyngeal cancer, thyroid cancer, pancreatic cancer, prostate cancer, adenocarcinoma, mouth cancer, esophageal cancer, squamous cell cancer and colon cancer.

One or more embodiments of the present application also provide the compounds of the present application or pharmaceutically acceptable salts, solvates, complexes or boric anhydride thereof, or the compounds of the present application, or stereoisomers, enantiomers, tautomers or mixtures thereof, or pharmaceutically acceptable salts, solvates or prodrugs thereof, or the above pharmaceutical preparation or the above pharmaceutical composition, which are used in a method for inhibiting protease.

Terms used in the technical solutions of the present application will be described below. As used in the specification and appended claims, unless stated otherwise, the terms in the present application have the following meanings:

The term "compound" includes all stereoisomers, geometric isomers and tautomers. As used herein, a "compound" may be asymmetric. For example, it has one or more stereoisomers. Unless otherwise stated, all stereoisomers include, for example, individual enantiomers and diastereomers, or other stereoisomers or mixtures thereof. Compounds containing asymmetric carbon atoms herein can be separated in optically active pure form or racemic form. Optically active pure form can be separated from racemic mixtures or synthesized by using chiral raw materials or chiral reagents. As used herein, a "compound" also includes geometric isomers, which means that the substituents on double bond or ring of a compound have different cis-trans isomerism without chirality. As used herein, a "compound" also includes tautomers. The tautomers can be derived from the exchange of a single bond with an adjacent double bond with migration of a proton.

Compounds herein, including intermediates and the compounds of formula (I), can also be isotopically labeled by replacing one or more atoms with atoms having different atomic mass or mass number. Such isotopically labeled (i.e., radiolabeled) compounds are considered to be within the scope of the present application. Examples of isotopes in the compound herein include isotopes of hydrogen, carbon, nitrogen, oxygen, phosphorus, sulfur, fluorine, chlorine and iodine, which have the same proton number but different mass number.

The term "halogen" refers to fluorine, chlorine, bromine or iodine.

The term "amino" refers to —NH$_2$.

The term "cyano" refers to —CN.

The term "nitro" refers to —NO$_2$.

The term "hydroxyl" refers to —OH.

The term "carboxyl" refers to —COOH.

"Mercapto" group refers to "—SH" group.

"Carbonyl" group refers to C=O group.

"Isocyanate group" refers to "—NCO" group.

"Thiocyano" group refers to "—CNS" group.

"Isothiocyano" group refers to "NCS" group.

"CA to CB" or "CA-CB" refers to the number of carbon atoms in alkyl, alkenyl or alkynyl, or the number of carbon atoms in aryl or heteroaryl, wherein "A" and "B" are integers. That is, alkyl, alkenyl, alkynyl, aryl and heteroaryl may contain "A" to "B" carbon atoms. Therefore, for example, "C$_1$ to C$_4$ alkyl" or "C$_1$-C$_4$ alkyl" group refers to all alkyl having 1 to 4 carbons, namely CH$_3$—, CH$_3$CH$_2$—, CH$_3$CH$_2$CH$_2$—, (CH$_3$)$_2$CH—, CH$_3$CH$_2$CH$_2$CH$_2$—, CH$_3$CH$_2$CH(CH$_3$)— and (CH$_3$)$_3$C—.

The term "alkyl" refers to a saturated aliphatic hydrocarbon group, and the term includes straight chain and branched chain hydrocarbon groups, for example, C$_1$-C$_{20}$ alkyl, preferably C$_1$-C$_6$ alkyl. C$_1$-C$_{20}$ alkyl refers to an alkyl having 1 to 20 carbon atoms, such as 1 carbon atom, 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms or 20 carbon atoms. Non-limiting examples of alkyl include methyl, ethyl, n-propyl, isopropyl, n-butyl, isobutyl, sec-butyl, tert-butyl, n-pentyl, neopentyl, n-hexyl, etc. The alkyl may be unsubstituted or substituted by one or more substituents including but not limited to alkyl, alkoxy, cyano, hydroxyl, carbonyl, carboxyl, aryl, heteroaryl, amino, halogen, sulfonyl, sulfinyl, phosphonyl, etc.

The term "alkenyl" refers to a hydrocarbon group containing one or more double bonds in a straight or branched hydrocarbon chain. The alkenyl may be substituted or unsubstituted. Alkenyl may have 1 to 20 carbon atoms, wherein the numerical range of "1 to 20" refers to each integer in the given range; for example, "1 to 20 carbon atoms" means that the alkenyl may contain 1 carbon atom, 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, or 20 carbon atoms.

The term "alkynyl" refers to a hydrocarbon group containing one or more triple bonds in a straight or branched hydrocarbon chain. The alkynyl may be substituted or unsubstituted. Alkynyl may have 1 to 20 carbon atoms, wherein the numerical range of "1 to 20" refers to each integer in the given range; for example, "1 to 20 carbon atoms" means that the alkynyl may contain 1 carbon atom, 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, or 20 carbon atoms.

The term "cycloalkyl" refers to cyclic alkyl with monocyclic or polycyclic rings (including fused ring, bridged ring and spiro ring systems), including cyclic alkyl composed of 3 to 8 carbon atoms (for example, 3, 4, 5, 6, 7 or 8 carbon atoms) and hydrogen atoms. Non-limiting examples of cycloalkyl include cyclopropyl, cyclobutyl, cyclopentyl, cyclohexyl, spiro[3.4]octyl, bicyclo[1.1.1]pentanyl, bicyclo[3.1.0]hexyl, etc.

The term "heterocycloalkyl" refers to saturated nonaromatic monocyclic, fused, bridged or spirocyclic rings containing one or more (e.g., 1, 2, 3 or 4) heteroatoms. Wherein, the heteroatom is typically N, O, S or

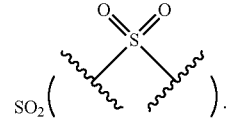

The heterocycloalkyl can be a 3 to 10 membered (e.g., containing 3, 4, 5, 6, 7, 8, 9 or 10 ring atoms) monocyclic, bicyclic or tricyclic ring. Examples of heterocyclic alkyl include but are not limited to piperazinyl, morpholinyl, piperidinyl, pyrrolidinyl, tetrahydrofuryl, tetrahydro-2H-pyranyl, etc. The heterocycloalkyl may be unsubstituted or substituted by one or more substituents including but not limited to halogen, alkyl, haloalkyl, amino, cyano, hydroxy, alkoxy, haloalkoxy, carbonyl, cycloalkyl, heterocycloalkyl, sulfonyl optionally substituted by C$_1$-C$_3$ alkyl, aryl and heteroaryl, etc.

The term "aryl" refers to an all-carbon monocyclic or all-carbon fused ring with a fully conjugated π-electron system, usually has 5 to 14 carbon atoms, for example, 6, 10, 12, 14 carbon atoms. The aryl may be unsubstituted or substituted by one or more substituents including, but not limited to alkyl, alkoxy, cyano, hydroxyl, carboxyl, aryl, aralkyl, amino, halogen, sulfonyl, sulfinyl and phosphonyl. Examples of unsubstituted aryl include, but are not limited to, phenyl, naphthyl and anthracenyl.

The term "heteroaryl" refers to a monocyclic or fused ring with 6 to 12 ring atoms (e.g., 6, 10, 12, 14 ring atoms) containing 1 to 4 (e.g., 1, 2, 3, or 4) heteroatoms being selected from the group consisting of N, O, and S, and the rest ring atom(s) are C. It has a fully conjugated π-electron system, and includes, but not limited to pyrrolyl, furyl, thienyl, imidazolyl, oxazolyl, isoxazolyl, pyrazolyl, pyridyl, pyrimidinyl, pyrazinyl, pyridazinyl, quinolinyl, isoquinolinyl, triazolyl, benzimidazolyl, benzotriazolyl, etc. The heteroaryl may be unsubstituted or substituted by one or more substituents including but not limited to alkyl, alkoxy, cyano, hydroxyl, carbonyl, carboxyl, aryl, aralkyl, amino, halogen, sulfonyl, sulfinyl and phosphonyl.

"Alkoxy" refers to —OR, wherein R is alkyl as defined herein. Non-limiting examples of alkoxy include methoxy, ethoxy, n-propoxy, 1-methylethoxy (isopropoxy), n-butoxy, isobutoxy, sec-butoxy and tert-butoxy. The alkoxy may be substituted or unsubstituted.

"Acyl" refers to a carbonyl connected with hydrogen, alkyl, alkenyl, alkynyl or aryl as substituents. Examples include formyl, acetyl, propionyl, benzoyl and acryloyl. The acyl may be substituted or unsubstituted.

"Haloalkyl" refers to an alkyl in which one or more hydrogen atoms are substituted by halogen (for example, monohaloalkyl, dihaloalkyl, and trihaloalkyl). Such groups include, but are not limited to, chloromethyl, fluoromethyl, difluoromethyl, trifluoromethyl, 1-chloro-2-fluoromethyl and 2-fluoroisobutyl. The haloalkyl may be substituted or unsubstituted.

"Haloalkoxy" refers to an alkoxy in which one or more hydrogen atoms are substituted by halogen (for example, monohaloalkoxy, dihaloalkoxy, and trihaloalkoxy). Such groups include, but are not limited to, chloromethoxy, fluoromethoxy, difluoromethoxy, trifluoromethoxy, 1-chloro-2-fluoromethoxy and 2-fluoroisobutoxy. The haloalkoxy may be substituted or unsubstituted.

"Arylthio" refers to RS—, wherein R is aryl, such as, but not limited to, phenyl. The arylthio may be substituted or unsubstituted.

"Thiocarbonyl" group refers to "—C(=S)R" group, wherein R is the same as the definition of R in O-carboxyl. The thiocarbonyl may be substituted or unsubstituted.

"Hydrocarbonylthio" group refers to "—SR" group, wherein R may be alkyl (alkylthio in this case), alkenyl, alkynyl, cycloalkyl, cycloalkenyl, cycloalkynyl, aryl, heteroaryl, heteroalicyclyl, aralkyl, (heteroaryl) alkyl or (heterocyclyl) alkyl. The hydrocarbonylthio may be substituted or unsubstituted.

"Sulfinyl" group refers to "—S(=O)—R" group, wherein R has the same definition as the R in alkylthio. The sulfinyl may be substituted or unsubstituted.

"Sulfonyl" group refers to the "$SO_2R$" group, wherein R has the same definition as the R in alkylthio. The sulfonyl may be substituted or unsubstituted.

"DMSO" refers to dimethyl sulfoxide.

"C-amido" group refers to a "C(=O)N($R_A R_B$)" group, wherein $R_A$ and $R_B$ may be independently hydrogen, alkyl, alkenyl, alkynyl, cycloalkyl, cycloalkenyl, cycloalkynyl, aryl, heteroaryl, heteroalicyclyl, aralkyl, (heteroaryl) alkyl or (heteroalicyclyl) alkyl. The C-amido may be substituted or unsubstituted.

"N-amido" group refers to "RC(=O)N($R_A$)" group, wherein R and $R_A$ may be hydrogen, alkyl, alkenyl, alkynyl, cycloalkyl, cycloalkenyl, cycloalkynyl, aryl, heteroaryl, heteroalicyclyl, aralkyl, (heteroaryl) alkyl or (heterocyclyl) alkyl. The N-amido may be substituted or unsubstituted.

"S-sulfonamido" group refers to a "—$SO_2$N($R_A R_B$)" group, wherein $R_A$ and $R_B$ may be independently hydrogen, alkyl, alkenyl, alkynyl, cycloalkyl, cycloalkenyl, cycloalkynyl, aryl, heteroaryl, heteroalicyclyl, aralkyl, (heteroaryl) alkyl or (heteroalicyclyl) alkyl. The S-sulfonamido may be substituted or unsubstituted.

"N-sulfonamido" group refers to "$RSO_2$N($R_A$)—" group, wherein R and $R_A$ may be hydrogen, alkyl, alkenyl, alkynyl, cycloalkyl, cycloalkenyl, cycloalkynyl, aryl, heteroaryl, heteroalicyclyl, aralkyl, (heteroaryl) alkyl or (heterocyclyl) alkyl. The N-sulfonamido may be substituted or unsubstituted.

"O-formamyl" group refers to a "—OC(=O)N($R_A R_B$)" group, wherein $R_A$ and $R_B$ may be independently hydrogen, alkyl, alkenyl, alkynyl, cycloalkyl, cycloalkenyl, cycloalkynyl, aryl, heteroaryl, heteroalicyclyl, aralkyl, (heteroaryl) alkyl or (heteroalicyclyl) alkyl. The O-formamyl may be substituted or unsubstituted.

"N-formamyl" group refers to "ROC(=O)N($R_A$)—" group, wherein R and $R_A$ may be hydrogen, alkyl, alkenyl, alkynyl, cycloalkyl, cycloalkenyl, cycloalkynyl, aryl, heteroaryl, heteroalicyclyl, aralkyl, (heteroaryl) alkyl or (heterocyclyl) alkyl. The N-formamyl may be substituted or unsubstituted.

"O-thiocarbamoyl" group refers to a "—OC(=S)—N($R_A R_B$)" group, wherein $R_A$ and $R_B$ may be independently hydrogen, alkyl, alkenyl, alkynyl, cycloalkyl, cycloalkenyl, cycloalkynyl, aryl, heteroaryl, heteroalicyclyl, aralkyl, (heteroaryl) alkyl or (heteroalicyclyl) alkyl. The O-thiocarbamoyl may be substituted or unsubstituted.

"N-thiocarbamoyl" group refers to "ROC(=S)N($R_A$)—" group, wherein R and $R_A$ may be hydrogen, alkyl, alkenyl, alkynyl, cycloalkyl, cycloalkenyl, cycloalkynyl, aryl, heteroaryl, heteroalicyclyl, aralkyl, (heteroaryl) alkyl or (heterocyclyl) alkyl. The N-thiocarbamoyl may be substituted or unsubstituted.

As used herein, the term "substituted" means that any group is monosubstituted or polysubstituted by a specified substituent to the extent that such monosubstitution or polysubstitution (including polysubstitution in the same part) is chemically permitted, and each substituent can be located at any available position on the group and can be connected by any available atom on the substituent. "Any available position" refers to any position on the group that can be chemically obtained by methods known in the art or taught herein and does not produce excessively unstable molecules. When there are two or more substituents on any group, each substituent is defined independently of any other substituents, so they can be the same or different.

When a group is described as "optionally substituted", the group may be unsubstituted or substituted by one or more of the following substituents: hydrogen, fluorine, chlorine, bromine, iodine, nitro, trifluoromethyl, difluoromethyl, difluoromethoxy, methoxy, acyl, alkoxy, heterocycloalkyl, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl) alkyl, hydroxyl, aryloxy, mercapto, alkylthio, arylthio, cyano, halogen, thiocarbonyl, O-carbamoyl, N-carbamoyl, O-thiocarbamoyl, N-thiocarbamoyl, C-amido, N-amido, S-sulfonamido, N-sulfonylamino, carboxyl, isocyanate group, thiocyanate group, isothiocyanate group, silyl, hydrocarbylthio, sulfinyl, sulfonyl, haloalkyl, haloalkoxy and amino.

As used herein, the term "unsubstituted or substituted" means that any group is monosubstituted or polysubstituted by a specified substituent to the extent that such monosubstitution or polysubstitution (including polysubstitution in the same part) is chemically permitted, and each substituent can be located at any available position on the group and can be connected by any available atom on the substituent. "Any available position" refers to any position on the group that can be chemically obtained by methods known in the art or taught herein and does not produce excessively unstable molecules. When there are two or more substituents on any group, each substituent is defined independently of any other substituents, so they can be the same or different. The substituent refers to a group selected from a group consisting of: hydrogen, fluorine, chlorine, bromine, iodine, nitro, trifluoromethyl, difluoromethyl, trifluoromethoxy, difluoromethoxy, methoxy, alkyl, acyl, alkoxy, cycloalkyl, heterocycloalkyl, aryl or heteroaryl, wherein the groups are defined herein.

The term "the compound of the present application" (unless otherwise specified) refers to the compounds claimed by the claims and all pure nitrogen oxides, sulfur oxides, solvates, isotopically labeled compounds and any pharmaceutically acceptable salts thereof. The solvates of the compound of the present application refer to compound or salts thereof stoichiometrically and non-stoichiometrically combined with solvents, such as hydrates, ethanol solvates, methanol solvates, etc. The compounds may also exist in one or more crystalline states, i.e. as a cocrystal or polymorph, or it may exist as an amorphous solid. All the above forms are covered by the claims.

The borate ester compound of the present application can further form salts, such as "pharmaceutically acceptable salts" derived from inorganic or organic acids. These include, but are not limited to, acetate, adipate, alginate, citrate, aspartate, benzoate, benzenesulfonate, bisulfate, butyrate, camphorate, camphorsulfonate, digluconate, cyclopentane propionate, dodecyl sulfate, ethanesulfonate, glucose heptanoate, glycerophosphate, hemisulphate, heptanoate, caproate, fumarate lactate, hydrochloride, hydrobromide, hydroiodide, 2-hydroxyethanesulfonate, lactate, maleate, methanesulfonate, hydrochloride, 2-naphthalenesulfonate, oxalate, pectinate, sulfate, 3-phenylpropionate, picrate, trimethyl acetate, propionate, succinate, tartrate, thiocyanate, p-toluenesulfonate and caprate. In addition, basic nitrogen-containing groups can be quaternized with the following reagents to generate quaternary ammonium salts: such as lower alkyl halides, including chlorides, bromides and iodides of methyl, ethyl, propyl and butyl; dialkyl sulfates including sulfates of dimethyl, diethyl, dibutyl and dipentyl; long chain halides including chloride, bromide and iodide of decyl, lauryl, myristyl and stearyl; aralkyl halides, such as bromides of benzyl and phenethyl, etc.

The present application also includes isotopically labeled compounds of the present application, that is, the same structure as that disclosed above, but one or more atoms in the structure are replaced by atoms with the same proton number but different neutron number. Examples of isotopes which can be combined with the compound of the present application include isotopes of hydrogen, carbon, oxygen, sulfur, fluorine, chlorine and iodine, such as $^2$H, $^3$H, $^{13}$C, $^{14}$C, $^{15}$N, $^{18}$O, $^{17}$O, $^{35}$S, $^{18}$F, $^{36}$Cl and $^{131}$I, etc.

The term "pharmaceutically acceptable" means that the substance or composition must be chemically and/or toxicologically compatible with the other ingredients constituting the preparation and/or the mammal treated with it.

The following compounds are also covered by one or more embodiments of the present application:

2-fluoro-5-bromo-N-[2-({(1R)-3-methyl-1-[(5R)-4-oxo-5-phenyl-1,3,2-dioxaborolan-2-yl]butyl}amino)-2-oxoethyl]benzamide; and 2-fluoro-5-bromo-N-[2-({(1R)-3-methyl-1-[(5S)-4-oxo-5-phenyl-1,3,2-dioxaborolan-2-yl]butyl}amino)-2-oxoehtyl]benzoyl; and the like, or salts, boric acid complex, borate esters or boric anhydride thereof.

"Pharmaceutical preparation" in the present application can be made by combining the pharmaceutical composition directly or with other active ingredients and pharmaceutical adjuvants or carriers. The preparation comprises tablets, pills, capsules, granules, suspensions, emulsions and the like. The pharmaceutical adjuvants or carriers include: binder such as microcrystalline cellulose, tragacanth or gelatin; excipients such as starch or lactose; dispersant such as alginic acid, Primogel or corn starch; lubricants such as magnesium stearate; glidants such as colloidal silica; sweeteners such as sucrose or saccharin; flavoring agent such as peppermint oil, methyl salicylate or orange flavor agent; non-aqueous solvents such as dimethyl sulfoxide, alcohol, propylene glycol, polyethylene glycol, vegetable oil such as olive oil, and injectable organic esters such as ethyl oleate; aqueous carrier such as a mixture of alcohol and water, a buffer medium and brine; preservatives; antibacterial agents; antioxidants; chelating agents; dyes; pigments and spices, etc.

The cancers described in one or more embodiments of the present application are specifically histiocytic lymphoma, non-small cell lung cancer, small cell lung cancer, lung adenocarcinoma, lung squamous cell carcinoma, pancreatic cancer, breast cancer, prostate cancer, liver cancer, gastric cancer, colon cancer, rectal cancer, ovarian cancer, cervical cancer, brain cancer, esophageal cancer, bone cancer, testicular cancer, melanoma, skin cancer, epithelial cell carcinoma, prostate cancer, nasopharyngeal cancer, mouth cancer, leukemia, plasmacytoma or mantle cell tumor, and any one or more of brain tumor, reproductive system tumor, lymphatic system tumor, digestive system tumor, respiratory system tumor, and skin tumor.

Other anti-tumor drugs that can form a pharmaceutical composition together with the compounds of the present application include cytotoxic drugs, hormone drugs, antimetabolite drugs, tumor targeting drugs, and adjuvant therapy drugs. Cytotoxic drugs are such as carboplatin, cisplatin, irinotecan, paclitaxel, fluorouracil, cytarabine, leradamine, and retinoic acid; hormone drugs, such as dexamethasone, fulvestrant, and tamoxifen. etc; anti-metabolic drugs, fluorouracil, methotrexate, furafluorouracil and cytarabine; molecular targeted drugs, such as imatinib, erlotinib, lapatinib, etc., and PARP inhibitor drugs, such as Olaparib, Rubraca, Zejula, etc.; adjuvant drugs, such as recombinant human granulocyte colony stimulating factor, erythropoietin, pamidronate disodium, zoledronic acid, etc. In addition, it also includes anti-tumor biological drugs, such as Keytruda, Opdiv, Tecentriq, Imfinzi, and Bavencio, etc.

The compounds in one or more embodiments of the present application have stronger activity than existing related borate esters compounds used as proteasome inhibitors. For example, compared to existing compounds (compounds 6a, 6c, MLN9708, etc.), the compounds of the present application have a stronger inhibitory effect on tumor tissues and a better inhibitory effect on tumor tissue proliferation.

The compounds in one or more embodiments of the present application have higher safety.

The compounds in one or more embodiments of the present application have better physicochemical properties and pharmaceutical prospects. For example, in the stability test, under the accelerated test conditions of high temperature and high humidity, the compounds of the present application have little change in the content of main drug components, less impurity generation and stable properties. In the dissolution experiment, the compounds of this application show good solubility.

BRIEF DESCRIPTION TO THE DRAWING

EMBODIMENTS

Figure 1:
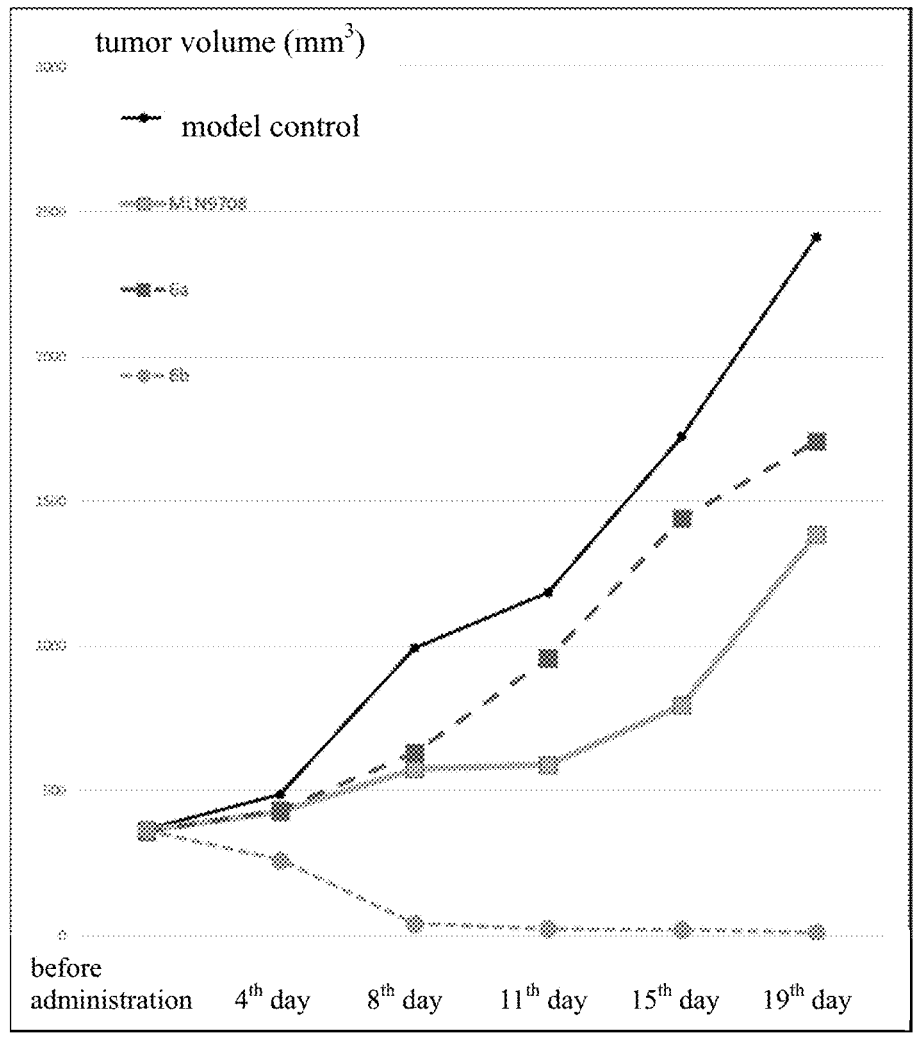
FIG. 1 shows the change of the average tumor volume of the transplantation tumor model of human multiple myeloma MM.1S in SCID mouse with the administration of various proteasome inhibitors.

The application is further explained with examples below, and the implementation details of the present application are given. However, it should be understood that the examples described below are exemplary, which are only used to explain the application, and cannot be understood as limiting the present application. For those skilled in the art, modification or substitution of the present application based on the prior art still fall within the protection scope of the present application. The reagents used in the examples of this application are all commercially available.

Preparation Example 1

Preparation of Compound 3b: 2-fluoro-5-bromo-N-[2-({(1R)-3-methyl-1-[(3aR,4R,6R,7aS)-3a,5,5-trimethylhexahydro-4,6-endo-methylene-1,3,2-benzodioxaborolan-2-yl]butyl}amino)-2-oxoethyl]benzamide

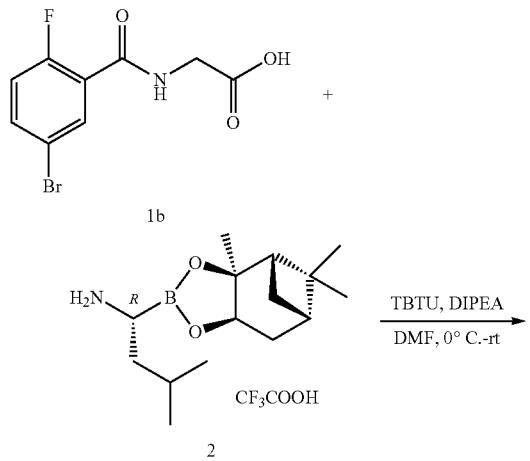

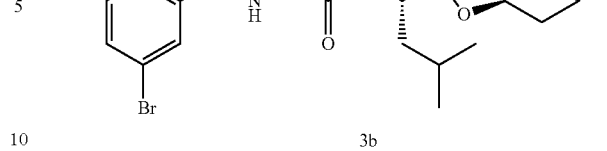

3b

In a 250 mL round-bottom flask, 8.28 g [(2-fluoro-5-bromobenzoyl) amino] acetic acid (compound 1b, 30.0 mmol) and 70 mL of DMF (N,N-dimethylformamide) were added thereto. The resultant mixture was stirred under ice bath condition for 10 min, then 10.60 g of TBTU (33.0 mmol, 1.10 eq) was added and stirred for 15 min, and then 12.0 g of (R)-1-[(3aS,4S,6S,7aR)-3a,5,5-trimethylhexahydro-4,6-endo-methylene-1,3,2-benzodioxaborolan-2-yl]-3-methyl-1-butylamino-2,2,2-trifluoroacetate (compound 2, 31.5 mmol, 1.05 eq.) was added and stirred under ice bath condition for 10 min. A mixture of 13.06 mL of DIPEA (75.0 mmol, 2.50 eq.) and 15 mL of DMF were dropwise added in about 15 min. After the dropping was finished, the reaction mixture was gradually warmed up to room temperature and reacted for about 4 h. TLC was used to monitor the reaction until the raw material 1b was consumed completely. After the reaction was completed, 150 mL of ethyl acetate was added into the reaction system to disperse the reaction mixture, and then 150 mL of water was added for extraction and liquid separation. The aqueous phase was reverse extracted once with 50 mL of ethyl acetate, and the ethyl acetate phases were combined and successively washed with 100 mL of 3% $K_2CO_3$ solution, 100 mL of 3% $H_3PO_4$ solution and 100 ml of 50% sodium chloride solution, and then the ethyl acetate organic phases were collected, dried with 50 g of anhydrous sodium sulfate for 1 h, and concentrated to dryness in vacuum to obtain a white solid product, namely, compound (3b): 2-fluoro-5-bromo-N-[2-({(1R)-3-methyl-1-[(3aR,4R,6R,7aS)-3a,5,5-trimethylhexahydro-4,6-endo-methylene-1,3,2-benzodioxaborolan-2-yl]butyl}amino)-2-oxoethyl]benzamide. Gross weight: 14.0 g; yield: 89.0%.

Preparation Example 2

Preparation of Compound 4b: [(1R)-1-({[(2-fluoro-5-bromo-benzoyl)amino]acetyl}amino)-3-methyl-butyl]boric acid

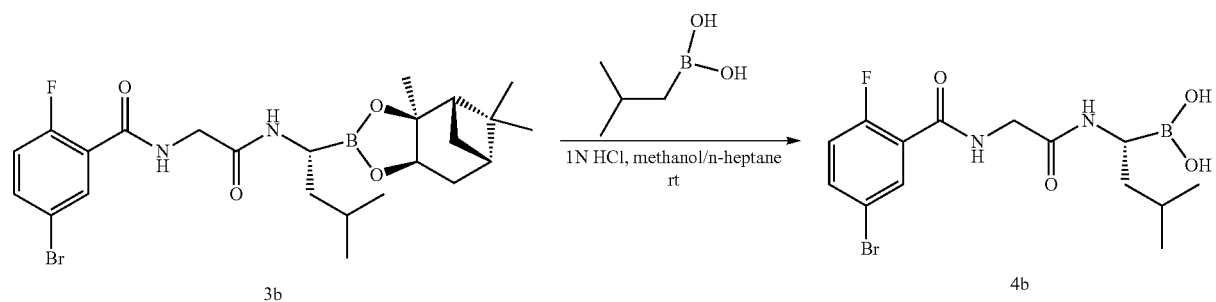

In a 250 mL round-bottom flask, 14.0 g (26.75 mmol) of the compound 3b obtained as above was dissolved by adding 70 mL of methanol under stirring. Then 70 mL of n-heptane and 5.45 g of isobutyl boric acid (53.5 mmol, 2.0 eq) were added under stirring at room temperature. After stirring for 15 min, 40.1 mL (40.12 mmol, 1.5 eq.) of 1N HCl solution was dropwise added in 20 min. After the dropping was finished, the reaction mixture was stirred violently at room temperature overnight, and TLC was used to monitor the reaction until the raw material 3b was consumed completely. After the reaction was completed, the reaction mixture was left to stand and formed two phases. The methanol phase was washed twice with 50 mL×2 n-heptane, then the methanol phase was collected and concentrated to ¼ volume. 50 mL of methylene chloride and 50 mL of water were added to the methanol phase under ice bath condition, and the resultant mixture was neutralized to alkalinity (pH was about 10) with 2N NaOH solution under stirring, extracted and separated. The aqueous phase was washed twice with 50 mL×2 methylene chloride and collected. Under the condition of ice bath, 80 mL of methylene chloride was added to the water phase, the resultant mixture was neutralized to weak acidity (pH was about 4) with 1N HCl solution, extracted and separated. The aqueous phase was washed twice with 50 mL×2 methylene chloride, and the methylene chloride phases were combined, washed once with 100 mL of 50% sodium chloride solution, dried with 50 g of anhydrous sodium sulfate for 1 h, and then concentrated in vacuum to very small volume. Then, 60 mL of n-heptane was added to the concentrated residual methylene chloride phase under stirring, and a lot of white solid was produced in the system. After suction filtration, the filter cake was dried to obtain white solid product, namely, compound 4b: [(1R)-1-({[(2-fluoro-5-bromo-benzoyl)amino]acetyl}amino)-3-methylbutyl]boric acid. Gross weight: 7.80 g, yield: 75.0%.

Preparation Example 3

Preparation of Compound 6b: (R)-2,2'-(2-(1-(2-(2-fluoro-5-bromo-benzoylamino)acetylamino)-3-methylbutyl)-5-oxo-1,3,2-dioxaborolan-4,4-diyl)diacetic acid

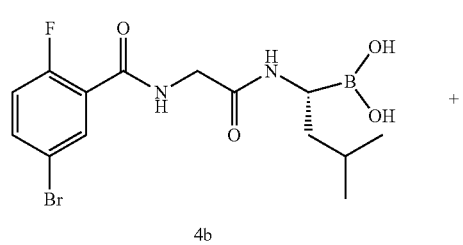

4b

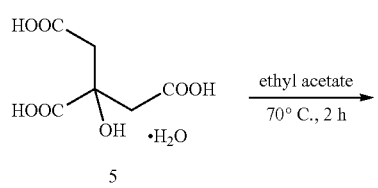

5

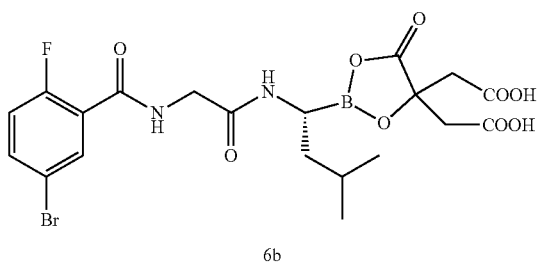

6b

In a 100 mL round-bottom flask, 1.56 g (4.0 mmol) of compound 4b obtained as above was dissolved by adding 20 mL of ethyl acetate under stirring. The resultant mixture was warmed to 70° C. and 0.84 g of citric acid monohydrate (compound 5, 4.0 mmol, 1.0 eq.) was added thereto under stirring. After reacting for 0.5 h, a white solid was produced in the system and the mixture was further reacted for 1 h under heating condition. The reaction mixture was cooled to room temperature, and subjected to suction filtration. The resultant white solid filter cake was washed twice with 15 mL×2 ethyl acetate, and suction-dried in an oil pump vacuum to obtain white solid product (6b): (R)-2,2'-(2-(1-(2-(2-fluoro-5-bromo-benzoylamino)acetylamino)-3-methylbutyl)-5-oxo-1,3,2-dioxaborolan-4,4-diyl)diacetic acid. Gross weight: 1.75 g, yield: 80.0%. $^1$H NMR (400 MHz, DMSO) δ=12.12 (s, 2H), 10.64 (s, 1H), 8.88 (dd, J=8.4, 5.2 Hz, 1H), 7.91 (dd, J=6.4, 2.8 Hz, 1H), 7.77 (m, 1H), 7.34 (t, 10.0 Hz, 1H), 4.42-4.18 (m, 2H), 2.89 (m, 1H), 2.82-2.51 (m, 4H), 1.68 (m, 1H), 1.44-1.08 (m, 2H), 0.86 (d, J=6.4 Hz, 6H). ESI-MS: $[C_{20}H_{23}BBrFN_2O_9$—H], calculated value: 544.12, measured value: 544.66; $[C_{20}H_{23}BBrFN_2O_9+Na^+]$, calculated value: 568.11; measured value: 568.69.

Preparation Example 4

Preparation of Compound 6d: 4-(R,S)-(carboxylmethyl)-2-((R)-1-(2-(2-fluoro-5-bromo-benzoylamino)acetylamino)-3-methylbutyl)-6-oxo-1,3,2-dioxaborolane-4-formic acid

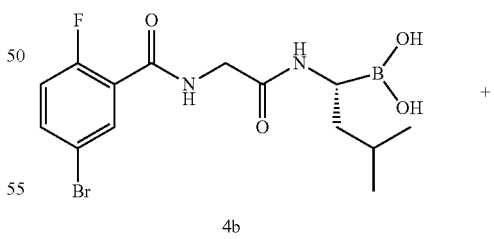

4b

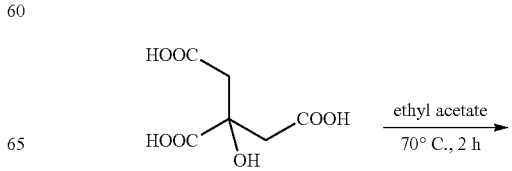

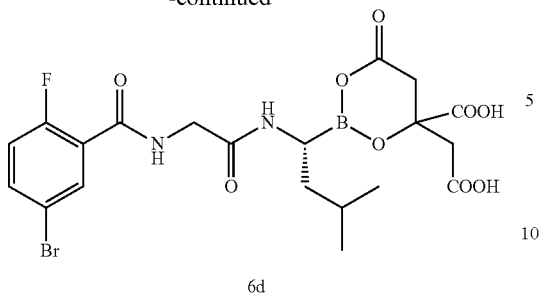

6d

In a round bottom flask, the compound 6d was prepared according to the method of Example 3, except that citric acid monohydrate was replaced by anhydrous citric acid, and other steps were carried out in the same way, thus obtaining compound 6d: 4-(R,S)-(carboxylmethyl)-2-((R)-1-(2-(2-fluoro-5-bromo-benzoylamino)acetylamino)-3-methylbutyl)-6-oxo-1,3,2-dioxaborolane-4-formic acid.

Or, the compound 6d can be prepared according to the method of Preparation Example 3, except that citric acid monohydrate was replaced by anhydrous citric acid, and the post-reaction treatment mode was adjusted accordingly.

In a 100 mL round-bottom flask, 1.56 g (4.0 mmol) of compound 4b was dissolved by adding 20 mL of ethyl acetate under stirring. The resultant solution was heated 70° C., then 0.77 g of anhydrous citric acid (4.0 mmol, 1.0 eq.) was added thereto under stirring. After stirring for 0.5 h, the mixture was slowly cooled (about 0.33° C./min) until the internal temperature was about 60° C. and the mixture was stirred for 2 h. Then, the resultant slurry was slowly cooled (about 0.12° C./min) until the internal temperature was about 25° C. and continued to stir overnight. A lot of white solid was precipitated in the reaction system, and then filtered by suction. The resultant white solid filter cake was washed twice with 15 mL×2 ethyl acetate, suction-dried in an oil pump vacuum to obtain white solid product (6d): 4-(R,S)-(carboxylmethyl)-2-((R)-1-(2-(2-fluoro-5-bromo-benzoylamino)acetylamino)-3-methylbutyl)-6-oxo-1,3,2-dioxaborolane-4-formic acid. Gross weight: 1.85 g, yield: 85.0%. $^1$H NMR (400 MHz, DMSO) δ=12.12 (s, 2H), 10.64 (s, 1H), 8.88 (dd, J=8.4, 5.2 Hz, 1H), 7.91 (dd, J=6.4, 2.8 Hz, 1H), 7.77 (m, 1H), 7.34 (t, 10.0 Hz, 1H), 4.42-4.18 (m, 2H), 2.89 (m, 1H), 2.82-2.51 (m, 4H), 1.68 (m, 1H), 1.44-1.08 (m, 2H), 0.86 (d, J=6.4 Hz, 6H). ESI-MS: [$C_{20}H_{23}BBrFN_2O_9$—H], calculated value: 544.12, measured value: 544.66; [$C_{20}H_{23}BBrFN_2O_9$+Na$^+$], calculated value: 568.11; measured value: 568.88.

Preparation Example 5

Preparation of Compound 6e: 2-fluoro-5-bromo-N-(2-{[(1R)-3-methyl-1-(4-oxo-4H-1,3,2-benzodioxaborolan-2-yl)butyl]amino}-2-oxoethyl)benzamide

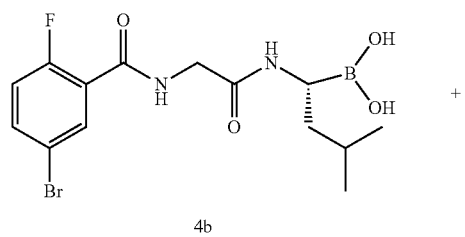

4b

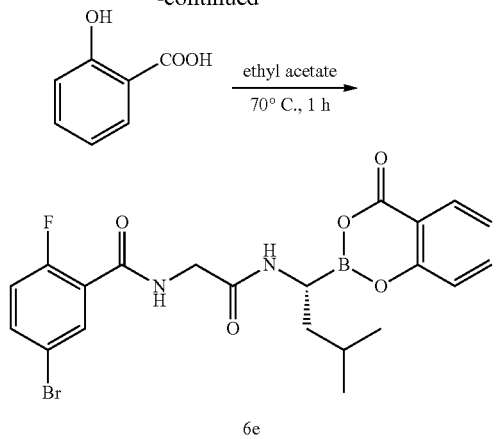

6e

In a 100 mL round-bottom flask, 1.17 g (3.0 mmol) of compound 4b was dissolved by adding 23 mL of ethyl acetate under stirring. The resultant mixture was warmed to 70° C. and 0.44 g of salicylic acid (3.15 mmol, 1.05 eq.) was added thereto under stirring. After reacting for 5 min, a lot of white solid was produced in the system and the mixture was further reacted for 1 h under heating condition. The reaction mixture was cooled to room temperature, and subjected to suction filtration. The resultant white solid filter cake was washed twice with 15 mL×2 ethyl acetate, and suction-dried in an oil pump vacuum to obtain white solid product (6e):

2-fluoro-5-bromo-N-(2-{[(1R)-3-methyl-1-(4-oxo-4H-1,3,2-benzodioxaborolan-2-yl)butyl]amino}-2-oxoethyl)benzamide. Gross weight: 1.22 g, yield: 83.0%. $^1$H NMR (400 MHz, DMSO) δ=10.89 (s, 1H), 8.94 (d, J=2.8 Hz, 1H), 7.87 (d, J=4.4 Hz, 1H), 7.78 (m, 2H), 7.54-7.42 (m, 1H), 7.34 (m, 1H), 6.94 (dd, J=15.4, 8.0 Hz, 2H), 4.28 (d, J=5.2 Hz, 2H), 2.90-2.72 (m, 1H), 1.65 (m, 1H), 1.52-1.32 (m, 2H), 0.88 (t, J=6.8 Hz, 6H). $^{13}$C NMR (101 MHz, DMSO) δ=176.44, 163.41, 160.46, 158.96, 157.95, 136.28, 135.60, 133.33, 129.73, 124.72, 120.30, 119.46, 119.22, 118.62, 116.56, 116.19, 39.01, 38.81, 26.01, 23.32, 22.71.

Preparation Example 6

Preparation of Compound 6f: 2-fluoro-5-bromo-N-[2-({(1R)-3-methyl-1-[4-oxo-5-phenyl-1,3,2-dioxaborolan-2-yl]butyl}amino)-2-oxoethyl]benzamide

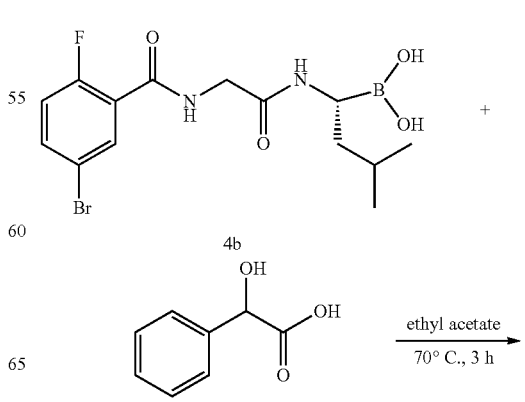

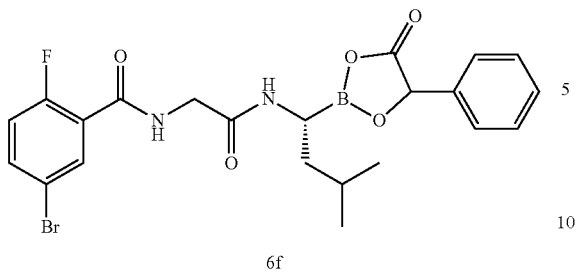

6f

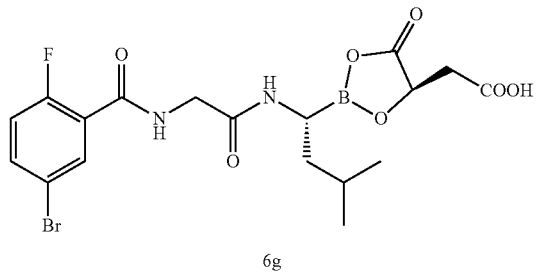

6g

In a 100 mL round-bottom flask, 1.17 g (3.0 mmol) of compound 4b was dissolved by adding 23 mL of ethyl acetate under stirring. The resultant mixture was warmed to 70° C. and 0.48 g of mandelic acid (3.15 mmol, 1.05 eq.) was added thereto under stirring. After reacting for 1 h, no solid was precipitated in the system and the mixture was cooled to room temperature and reacted for 2 h. 30 mL of n-heptane was added to the mixture, then a lot of white solid was obtained and the mixture was continued to stir for 0.5 h. Then, the mixture was subjected to suction filtration. The resultant white solid filter cake was washed twice with 15 mL×2 n-heptane, and dried in vacuum to obtain white solid product (6f): 2-fluoro-5-bromo-N-[2-({(1R)-3-methyl-1-[4-oxo-5-phenyl-1,3,2-dioxaborolan-2-yl]butyl}amino)-2-oxo-ethyl]benzamide. Gross weight: 1.42 g, yield: 93.4%. $^1$H NMR (400 MHz, DMSO) δ=10.88 (s, 1H), 9.02 (s, 1H), 7.93 (s, 1H), 7.81 (d, J=3.5 Hz, 1H), 7.53-7.23 (m, 6H), 5.19 (m, J=27.7 Hz, 1H), 4.47-4.28 (m, 2H), 2.80 (d, J=7.2 Hz, 1H), 1.67 (m, 1H), 1.56-1.26 (m, 2H), 0.91 (d, J=6.4 Hz, 6H). $^{13}$C NMR (101 MHz, DMSO) δ=176.75, 163.36, 160.54, 158.03, 139.77, 136.36, 133.31, 128.42, 127.91, 126.53, 124.73, 119.53, 119.29, 116.66, 76.62, 75.67, 39.06, 26.20, 25.92, 23.38, 22.51.

Preparation Example 7

Preparation of Compound 6g: {(4S)-2-[(1R)-1-({[(2-fluoro-5-bromobenzoyl)amino]-acetyl}amino)-3-methylbutyl]-5-oxo-1,3,2-dioxaborolan-4-yl}acetic acid

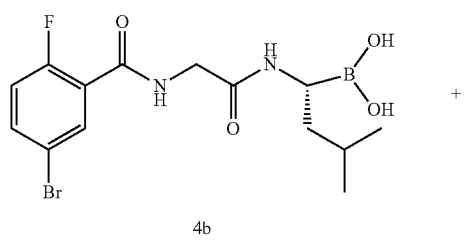

In a 100 mL round-bottom flask, 1.17 g (3.0 mmol) of compound 4b was dissolved by adding 23 mL of ethyl acetate under stirring. The resultant mixture was warmed to 70° C. and 0.40 g of L-malic acid (3.0 mmol, 1.0 eq.) was added thereto under stirring. After reacting for 1 h under heating condition, no solid was precipitated in the system and the mixture was cooled to room temperature and reacted for 2 h. Finally, the mixture was concentrated to dryness and suction-dried in an oil pump vacuum to obtain a lot of foam shaped solid which was washed twice with 15 mL×2 n-heptane, and suction-dried in an oil pump vacuum to obtain white solid product (6 g): {(4S)-2-[(1R)-1-({[(2-fluoro-5-bromobenzoyl)amino]-acetyl}amino)-3-methylbutyl]-5-oxo-1,3,2-dioxaborolan-4-yl}acetic acid. Gross weight: 1.34 g, yield: 92.0%. $^1$H NMR (400 MHz, DMSO) δ=12.34 (s, 1H), 10.81 (s, 1H), 9.17 (t, J=5.6 Hz, 1H), 7.89 (m, 1H), 7.68 (dd, J=8.6, 2.4 Hz, 1H), 7.48 (d, J=8.6 Hz, 1H), 4.43 (m, 1H), 4.32 (d, J=4.5 Hz, 2H), 2.66 (d, J=16.1 Hz, 2H), 2.45 (m, 1H), 1.68 (m, 1H), 1.52-1.26 (m, 2H), 1.01-0.75 (m, 6H).

Preparation Example 8

Preparation of Compound 6h: 4-(R,S)-(carboxylmethyl)-2-((R)-1-(2-(2-bromo-5-fluoro-benzoylamino)acetylamino)-3-methylbutyl)-6-oxo-1,3,2-dioxaborolan-4-formic acid

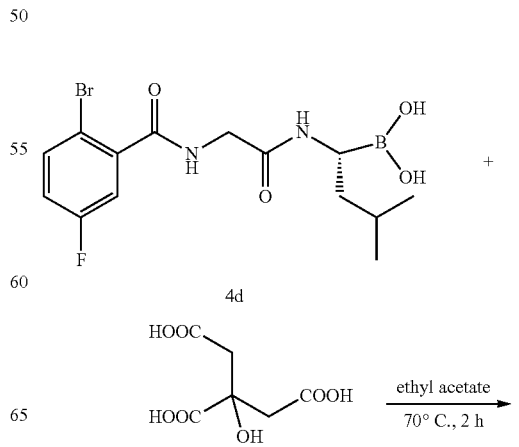

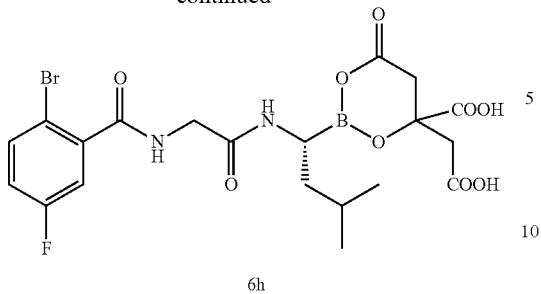

6h

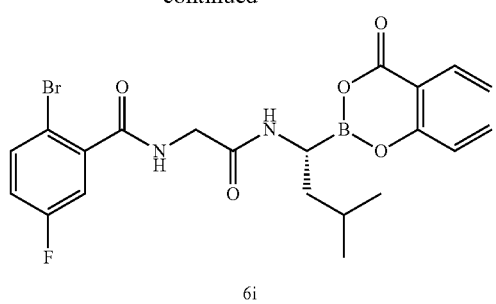

6i

Compound 4d was prepared according to the method of Preparation Example 1, except that [(2-fluoro-5-bromobenzoyl)amino]acetic acid was replaced by [(2-bromo-5-fluorobenzoyl)amino]acetic acid;

Compound 6h was prepared according to the method of Preparation Example 4, except that [(1R)-1-({[(2-fluoro-5-bromo-benzoyl)amino]acetyl}amino)-3-methylbutyl]boric acid was replaced by [(1R)-1-({[(2-bromo-5-fluoro-benzoyl)amino]acetyl}amino)-3-methylbutyl]boric acid.

In a 100 mL round-bottom flask, 1.56 g (4.0 mmol) of compound 4d was dissolved by adding 20 mL of ethyl acetate under stirring. The resultant solution was heated 70° C., then 0.77 g of citric acid (4.0 mmol, 1.0 eq.) was added thereto under stirring. After stirring for 0.5 h, the mixture was slowly cooled (about 0.33° C./min) until the internal temperature was about 60° C. and the mixture was stirred for 2 h. Then, the resultant slurry was slowly cooled (about 0.12° C./min) until the internal temperature was about 25° C. and continued to stir overnight. A lot of white solid was precipitated in the reaction system, and then filtered by suction. The resultant white solid filter cake was washed twice with 15 mL×2 ethyl acetate, suction-dried in an oil pump vacuum to obtain white solid product (6 h): 4-(R,S)-(carboxylmethyl)-2-((R)-1-(2-(2-bromo-5-fluoro-benzoylamino)acetylamino)-3-meth ylbutyl)-6-oxo-1,3,2-dioxaborolane-4-formic acid. Gross weight: 1.70 g, yield: 78.0%. $^1$H NMR (400 MHz, DMSO) δ=12.12 (s, 2H), 10.64 (s, 1H), 8.88 (dd, J=8.4, 5.2 Hz, 1H), 7.91 (dd, J=6.4, 2.8 Hz, 1H), 7.77 (m, 1H), 7.34 (t, 10.0 Hz, 1H), 4.42-4.18 (m, 2H), 2.89 (m, 1H), 2.82-2.51 (m, 4H), 1.68 (m, 1H), 1.44-1.08 (m, 2H), 0.86 (d, J=6.4 Hz, 6H).

Preparation Example 9

Preparation of Compound 6i: 2-bromo-5-fluoro-N-(2-{[(1R)-3-methyl-1-(4-oxo-4H-1,3,2-benzodioxaborolan-2-yl)butyl]amino}-2-oxoethyl)benzamide Compound 6i was prepared according to the method of Preparation Example 5, except that [(1R)-1-({[(2-fluoro-5-bromo-benzoyl)amino]acetyl}amino)-3-methylbutyl]boric acid was replaced by [(1R)-1-({[(2-bromo-5-fluoro-benzoyl)amino]acetyl}amino)-3-methylbutyl]boric acid.

In a 100 mL round-bottom flask, 1.17 g (3.0 mmol) of compound 4d was dissolved by adding 23 mL of ethyl acetate under stirring. The resultant mixture was warmed to 70° C. and 0.44 g of salicylic acid (3.15 mmol, 1.05 eq.) was added thereto under stirring. After reacting for 5 min, a lot of white solid was produced in the system and the mixture was further reacted for 1 h under heating condition. The reaction mixture was cooled to room temperature, and subjected to suction filtration. The resultant white solid filter cake was washed twice with 15 mL×2 ethyl acetate, and suction-dried in an oil pump vacuum to obtain white solid product (6i): 2-bromo-5-fluoro-N-(2-{[(1R)-3-methyl-1-(4-oxo-4H-1,3,2-benzodioxaborolan-2-yl)butyl]amino}-2-oxoethyl)benzamide. Gross weight: 1.20 g, yield: 81.6%. $^1$H NMR (400 MHz, DMSO) δ=10.89 (s, 1H), 8.94 (d, J=2.8 Hz, 1H), 7.87 (d, J=4.4 Hz, 1H), 7.78 (m, 2H), 7.54-7.42 (m, 1H), 7.34 (m, 1H), 6.94 (dd, J=15.4, 8.0 Hz, 2H), 4.28 (d, J=5.2 Hz, 2H), 2.90-2.72 (m, 1H), 1.65 (m, 1H), 1.52-1.32 (m, 2H), 0.88 (t, J=6.8 Hz, 6H).

Preparation Example 10

Preparation of Compound 6j: 2-bromo-5-fluoro-N-[2-({(1R)-3-methyl-1-[4-oxo-5-phenyl-1,3,2-dioxaborolan-2-yl]butyl}amino)-2-oxoethyl]benzamide

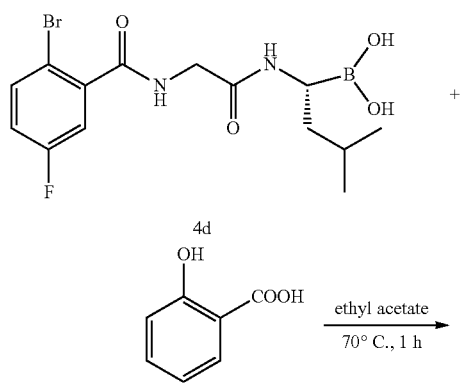

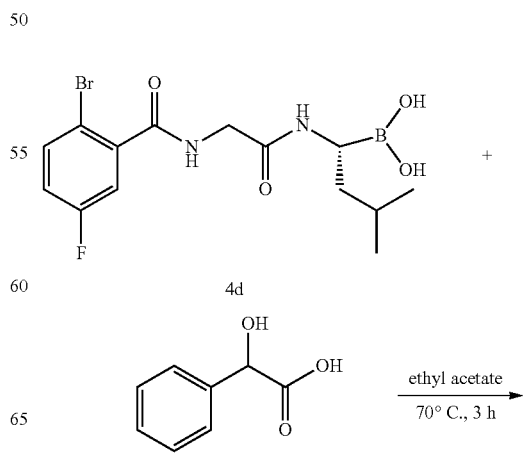

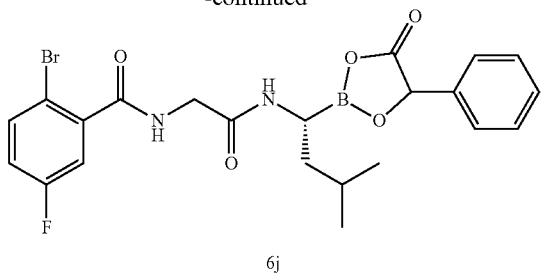

6j

Compound 6j was prepared according to the method of Preparation Example 6, except that [(1R)-1-({[(2-fluoro-5-bromo-benzoyl)amino]acetyl}amino)-3-methylbutyl]boric acid was replaced by [(1R)-1-({[(2-bromo-5-fluoro-benzoyl)amino]acetyl}amino)-3-methylbutyl]boric acid.

A white solid product (6j) can be obtained: 2-bromo-5-fluoro-N-[2-({(1R)-3-methyl-1-[4-oxo-5-phenyl-1,3,2-dioxaborolan-2-yl]butyl}amino)-2-oxoethyl]benzamide: $^1$H NMR (400 MHz, DMSO) δ=10.88 (s, 1H), 9.02 (s, 1H), 7.93 (s, 1H), 7.71-7.25 (m, 7H), 5.19 (m, J=27.7 Hz, 1H), 4.47-4.28 (m, 2H), 2.80 (d, J=7.2 Hz, 1H), 1.67 (m, 1H), 1.56-1.26 (m, 2H), 0.91 (d, J=6.4 Hz, 6H).

Preparation Example 11

Preparation of Compound 6k: {(4S)-2-[(1R)-1-({[(2-bromo-5-fluoro-benzoyl)amino]-acetyl}amino)-3-methylbutyl]-5-oxo-1,3,2-dioxaborolan-4-yl}acetic acid

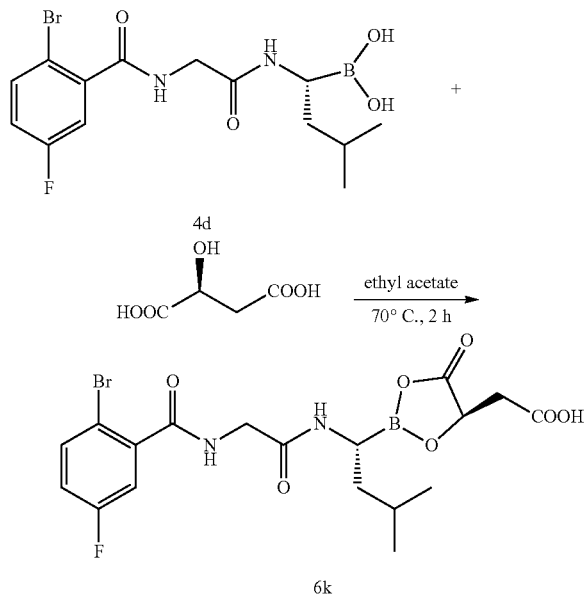

6k

Compound 6k was prepared according to the method of Preparation Example 7, except that [(1R)-1-({[(2-fluoro-5-bromo-benzoyl)amino]acetyl}amino)-3-methylbutyl]boric acid was replaced by [(1R)-1-({[(2-bromo-5-fluoro-benzoyl)amino]acetyl}amino)-3-methylbutyl]boric acid.

A white foamy solid product (6k) can be obtained: {(4S)-2-[(1R)-1-({[(2-bromo-5-fluoro-benzoyl)amino]-acetyl}amino)-3-methylbutyl]-5-oxo-1,3,2-dioxaborolan-4-yl}acetic acid: $^1$H NMR (400 MHz, DMSO) δ=12.34 (s, 1H), 10.81 (s, 1H), 9.20 (m, 1H), 7.89 (m, 1H), 7.68 (m, 1H), 7.48 (d, J=8.6 Hz, 1H), 4.43 (m, 1H), 4.32 (d, J=4.5 Hz, 2H), 2.66 (d, J=16.1 Hz, 2H), 2.45 (m, 1H), 1.68 (m, 1H), 1.52-1.26 (m, 2H), 1.01-0.75 (d, J=6.4 Hz, 6H).

Preparation Example 12

Preparation of Compound 6l: (R)-2,2'-(2-(1-(2-(2-bromo-5-fluoro-benzoylamino)acetylamino)-3-methylbutyl)-5-oxo-1,3,2-dioxaborolan-4,4-diyl)diacetic acid Compound 6l was prepared according to the method of Preparation Example 3, except that [(1R)-1-({[(2-fluoro-5-bromo-benzoyl)amino]acetyl}amino)-3-methylbutyl]boric acid was replaced by [(1R)-1-({[(2-bromo-5-fluoro-benzoyl)amino]acetyl}amino)-3-methylbutyl]boric acid.

A white solid product (6l) can be obtained: (R)-2,2'-(2-(1-(2-(2-bromo-5-fluoro-benzoylamino)acetylamino)-3-methylbutyl)-5-oxo-1,3,2-dioxaborolan-4,4-diyl)diacetic acid: $^1$H NMR (400 MHz, DMSO) δ=12.12 (s, 2H), 10.64 (s, 1H), 8.90 (m, 1H), 7.95 (dd, J=6.4, 2.8 Hz, 1H), 7.77 (m, 1H), 7.34 (m, 1H), 4.42-4.18 (m, 2H), 2.89 (m, 1H), 2.82-2.51 (m, 4H), 1.68 (m, 1H), 1.44-1.08 (m, 2H), 0.90 (d, J=6.4 Hz, 6H).

Preparation Example 13

Preparation of Compound 6m: 4-(R,S)-(carboxylmethyl)-2-((R)-1-(2-(2-fluoro-5-chloro-benzoylamino)acetylamino)-3-methylbutyl)-6-oxo-1,3,2-dioxaborolane-4-formic acid

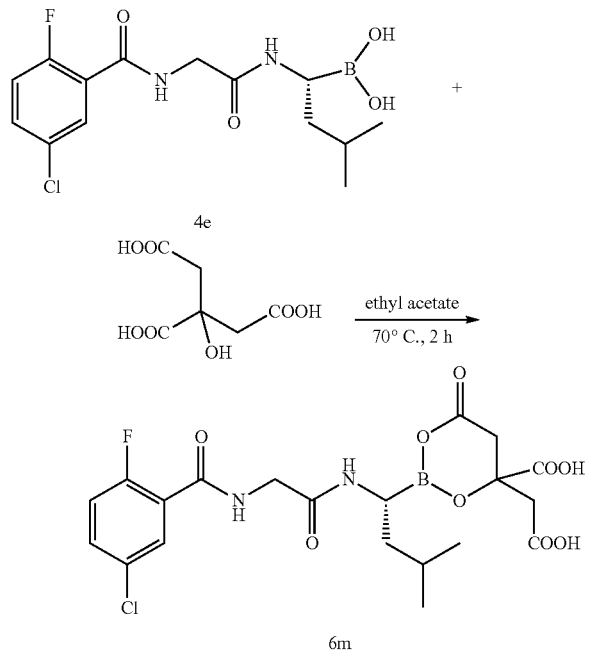

6m

Compound 6m was prepared according to the method of Preparation Example 4, except that [(1R)-1-({[(2-fluoro-5-bromo-benzoyl)amino]acetyl}amino)-3-methylbutyl]boric acid was replaced by [(1R)-1-({[(2-fluoro-5-chloro-benzoyl)amino]acetyl}amino)-3-methylbutyl]boric acid.

A white solid product (6m) can be obtained: 4-(R,S)-(carboxylmethyl)-2-((R)-1-(2-(2-fluoro-5-chloro-benzoylamino)acetylamino)-3-meth ylbutyl)-6-oxo-1,3,2-dioxaborolane-4-formic acid: $^1$H NMR (400 MHz, DMSO) δ=12.16 (s, 2H), 10.66 (s, 1H), 8.90 (d, J=2.8 Hz, 1H), 7.90 (m, 1H), 7.77 (m, 1H), 7.49-7.33 (m, 1H), 4.29 (s, 2H), 2.88 (m, 1H), 2.74-2.51 (m, 4H), 1.67 (s, 1H), 1.41-1.12 (m, 2H), 0.85 (d, J=6.4 Hz, 6H).

Preparation Example 14

Preparation of Compound 6n: 2-fluoro-5-chloro-N-(2-{[(1R)-3-methyl-1-(4-oxo-4H-1,3,2-benzodioxaborolan-2-yl)butyl]amino}-2-oxoethyl)benzamide

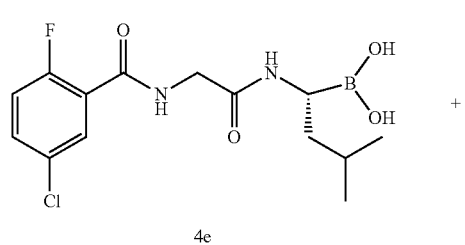

4e

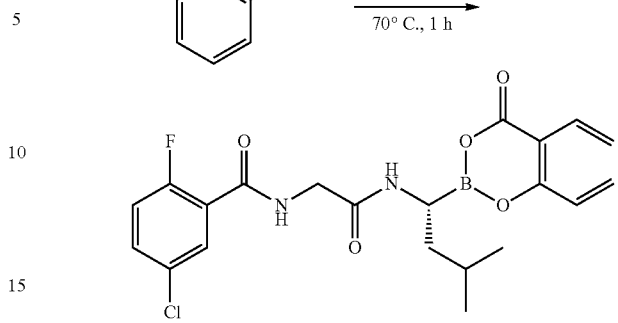

6n

Compound 6n was prepared according to the method of Preparation Example 5, except that [(1R)-1-({[(2-fluoro-5-bromo-benzoyl)amino]acetyl}amino)-3-methylbutyl]boric acid was replaced by [(1R)-1-({[(2-fluoro-5-chloro-benzoyl)amino]acetyl}amino)-3-methylbutyl]boric acid.

A white solid product (6n) can be obtained: 2-fluoro-5-chloro-N-(2-{[(1R)-3-methyl-1-(4-oxo-4H-1,3,2-benzodioxaborolan-2-yl)butyl]amino}-2-oxoethyl)benzamide: $^1$H NMR (400 MHz, DMSO) δ=10.89 (s, 1H), 9.05 (d, J=2.8 Hz, 1H), 7.90 (d, J=4.4 Hz, 1H), 7.78 (m, 2H), 7.54-7.42 (m, 1H), 7.34 (m, 1H), 6.96 (m, 2H), 4.28 (d, J=5.2 Hz, 2H), 2.90-2.72 (m, 1H), 1.65 (m, 1H), 1.52-1.32 (m, 2H), 0.85 (d, J=6.4 Hz, 6H).

Preparation Example 15

Preparation of Compound 6o: 2-fluoro-5-chloro-N-[2-({(1R)-3-methyl-1-[4-oxo-5-phenyl-1,3,2-dioxaborolan-2-yl]butyl}amino)-2-oxoethyl]benzamide

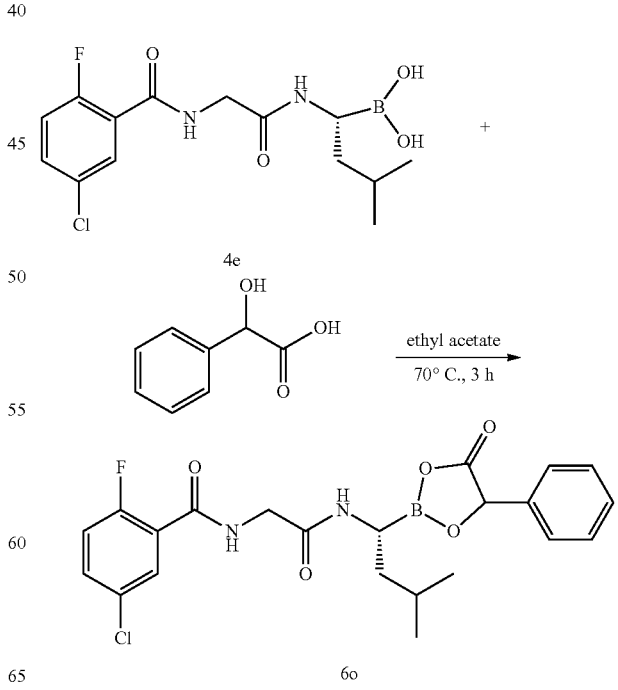

6o

Compound 6o was prepared according to the method of Preparation Example 6, except that [(1R)-1-({[(2-fluoro-5-bromo-benzoyl)amino]acetyl}amino)-3-methylbutyl]boric acid was replaced by [(1R)-1-({[(2-fluoro-5-chloro-benzoyl)amino]acetyl}amino)-3-methylbutyl]boric acid.

A white solid product (60) can be obtained: 2-fluoro-5-chloro-N-[2-({(1R)-3-methyl-1-[4-oxo-5-phenyl-1,3,2-dioxaborolan-2-yl]butyl}amino)-2-oxoethyl]benzamide: $^1$H NMR (400 MHz, DMSO) δ=10.88 (s, 1H), 8.95 (s, 1H), 7.93 (s, 1H), 7.80-7.28 (m, 7H), 5.19 (m, J=27.7 Hz, 1H), 4.47-4.28 (m, 2H), 2.80 (d, J=7.2 Hz, 1H), 1.67 (m, 1H), 1.56-1.26 (m, 2H), 0.95 (d, J=6.4 Hz, 6H).

Preparation Example 16

Preparation of Compound 6p: {(4S)-2-[(1R)-1-({[(2-fluoro-5-chloro-benzoyl)amino]-acetyl}amino)-3-methylbutyl]-5-oxo-1,3,2-dioxaborolan-4-yl}acetic acid

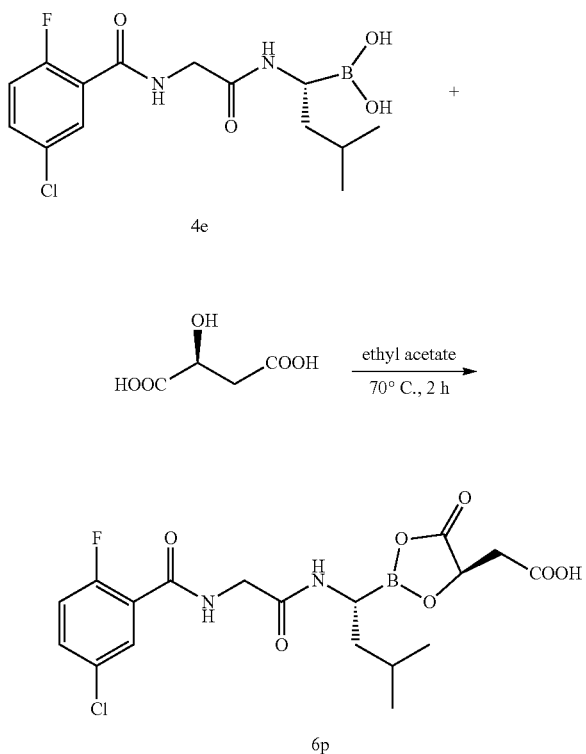

Compound 6p was prepared according to the method of Preparation Example 7, except that [(1R)-1-({[(2-fluoro-5-bromo-benzoyl)amino]acetyl}amino)-3-methylbutyl]boric acid was replaced by [(1R)-1-({[(2-fluoro-5-chloro-benzoyl)amino]acetyl}amino)-3-methylbutyl]boric acid.

A white foamy solid product (6p) can be obtained: {(4S)-2-[(1R)-1-({[(2-fluoro-5-chloro-benzoyl)amino]-acetyl}amino)-3-methylbutyl]-5-oxo-1,3,2-dioxaborolan-4-yl}acetic acid: $^1$H NMR (400 MHz, DMSO) δ=12.38 (s, 1H), 10.81 (s, 1H), 9.20 (m, 1H), 7.89 (m, 1H), 7.68 (m, 1H), 7.48 (d, J=8.6 Hz, 1H), 4.43 (m, 1H), 4.32 (d, J=4.5 Hz, 2H), 2.65-2.45 (m, 3H), 1.68 (m, 1H), 1.52-1.26 (m, 2H), 1.05-0.85 (d, J=6.4 Hz, 6H).

Preparation Example 17: Preparation of Compound 6q: (R)-2,2'-(2-(1-(2-(2-fluoro-5-chloro-benzoylamino)acetylamino)-3-methylbutyl)-5-oxo-1,3,2-dioxaborolan-4,4-diyl)diacetic acid Step 1: Preparation of Compound 3q: 2-fluoro-5-chloro-N-[2-({(1R)-3-methyl-1-[(3aR,4R,6R,7aS)-3a,5,5-trimethylhexahydro-4,6-endo-methylene-1,3,2-benzodioxaborolan-2-yl]butyl}amino)-2-oxoethyl]benzamide

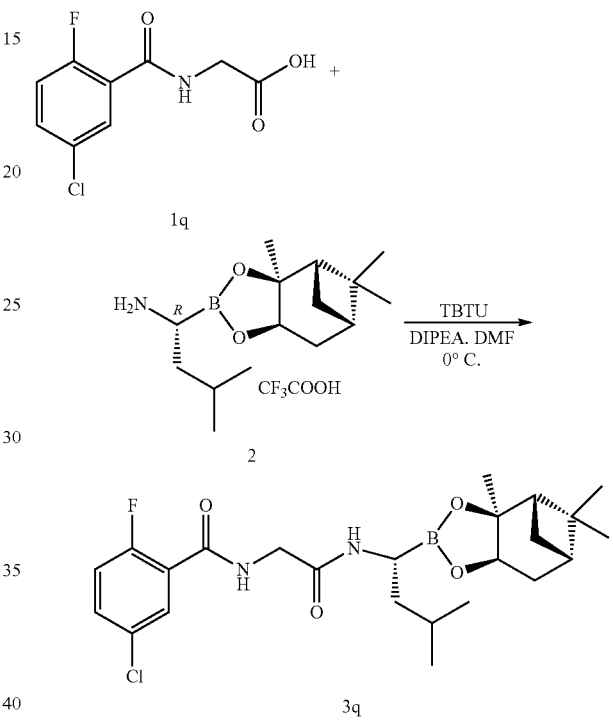

In a 100 mL round-bottom flask, 5.79 g [(2-fluoro-5-chlorobenzoyl) amino] acetic acid (compound 1q, 25.0 mmol) and 29 mL of DMF (N, N-dimethylformamide) were added thereto. The resultant mixture was stirred under ice bath condition for 10 min, then 9.63 g of TBTU (30.0 mmol, 1.20 eq) was added and stirred for 15 min, and then 9.95 g of (R)-1-[(3aS,4S,6S,7aR)-3a,5,5-trimethylhexahydro-4,6-endo-methylene-1,3,2-benzodioxaborolan-2-yl]-3-methyl-1-butylamino-2,2,2-trifluoroacetate (compound 2, 26.25 mmol, 1.05 eq.) was added and stirred under ice bath condition for 10 min. 10.89 mL of DIPEA (62.50 mmol, 2.50 eq.) was dropwise added in about 15 min. After the dropping was finished, the reaction mixture was gradually warmed up to room temperature and reacted for about 4 h. TLC was used to monitor the reaction until the raw material 1q was consumed completely. After the reaction was completed, 60 mL of ethyl acetate was added into the reaction system to dispersed the reaction mixture, and then 40 mL of water was added for extraction and liquid separation. The aqueous phase was reverse extracted once with 50 mL of ethyl acetate, and the ethyl acetate phases were combined. The resultant ethyl acetate phase was successively washed with 80 mL of 3% $K_2CO_3$ solution, 80 mL of 3% $H_3PO_4$ solution and 80 ml of 50% sodium chloride solution, and then the ethyl acetate organic phases were collected, dried with 50 g of anhydrous sodium sulfate for 1 h, and concentrated to dryness in vacuum to obtain a white solid product, namely, compound (3q): 2-fluoro-5-chloro-N-[2-({(1R)-3-methyl-1-[(3aR,4R,6R,7aS)-3a,5,5-trimethylhexahydro-4,6-endo-methylene-1,3,2-benzodioxaborolan-2-yl]butyl}amino)-2-oxoethyl]benzamide, which was directly used in the next reaction without purification.

Preparation of Compound 4e: [(1R)-1-({[(2-fluoro-5-chloro-benzoyl)amino]acetyl}amino)-3-methyl-butyl]boric acid

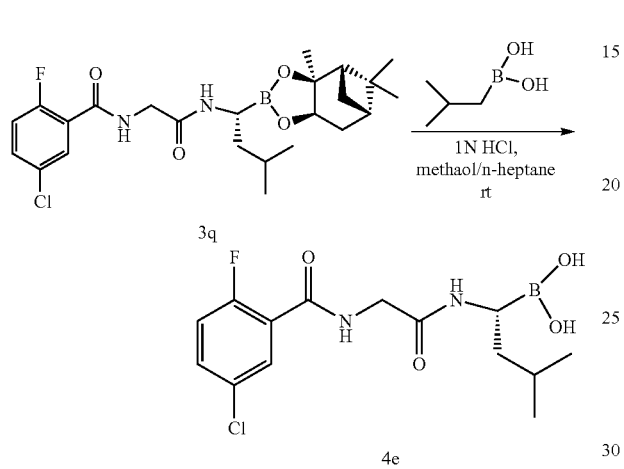

In a 250 mL round-bottom flask, the crude product of compound 3q obtained as above was dissolved by adding 58 mL of methanol under stirring. Then 48 mL of n-heptane and 3.82 g of isobutyl boric acid (37.50 mmol, 1.5 eq) were added under stirring at room temperature. After stirring for 15 min, 37.50 mL (37.50 mmol, 1.5 eq.) of 1N HCl solution was dropwise added in about 15 min. After the dropping was finished, the reaction mixture was stirred violently at room temperature overnight, and TLC was used to monitor the reaction until the raw material 3q was consumed completely. After the reaction was completed, the reaction mixture was left to stand and formed two phases. The methanol phase was washed twice with 50 mL×2 n-heptane, then the methanol phase was collected and concentrated to ¼ volume. 50 mL of methylene chloride and 50 mL of water were added to the methanol phase under ice bath condition, and the resultant mixture was neutralized to alkalinity (pH was about 10) with 2N NaOH solution under stirring, extracted and separated. The aqueous phase was washed twice with 50 mL×2 methylene chloride and collected. Under the condition of ice bath, 80 mL of methylene chloride was added to the water phase, the resultant mixture was neutralized to weak acidity (pH was about 4) with 1N HCl solution, extracted and separated. The aqueous phase was washed twice with 50 mL×2 methylene chloride, and the methylene chloride phases were combined, washed once with 100 mL of 50% sodium chloride solution, dried with 50 g of anhydrous sodium sulfate for 1 h, and then the methylene chloride phase was concentrated in vacuum to very small volume. Then, 60 mL of n-heptane was added to the concentrated residual methylene chloride phase under stirring, and a lot of white solid was produced in the system. After suction filtration, the filter cake was dried to obtain white solid product, namely, compound 4e: [(1R)-1-({[(2-fluoro-5-chloro-benzoyl)amino]acetyl}amino)-3-methylbutyl]boric acid. Gross weight: 6.26 g, yield: 72.7%.

Step 3: Preparation of Compound 6q: (R)-2,2'-(2-(1-(2-(2-fluoro-5-chloro-benzoylamino)acetylamino)-3-methylbutyl)-5-oxo-1,3,2-dioxaborolan-4,4-diyl)diacetic acid In a 100 mL round-bottom flask, 1.72 g (5.0 mmol) of compound 4e was dissolved by adding 35 mL of ethyl acetate under stirring. The resultant mixture was warmed to 70° C. and 1.07 g of citric acid monohydrate (compound 5, 5.10 mmol, 1.02 eq.) was added thereto under stirring. After reacting for about 5 min, a white solid was produced in the system and the mixture was further reacted for 2 h under heating condition. The reaction mixture was cooled to room temperature, and subjected to suction filtration. The resultant white solid filter cake was washed twice with 15 mL×2 ethyl acetate, and suction-dried in an oil pump vacuum to obtain white solid product (6q): (R)-2,2'-(2-(1-(2-(2-fluoro-5-chloro-benzoylamino)acetylamino)-3-methylbutyl)-5-oxo-1,3,2-dioxaborolan-4,4-diyl)diacetic acid. Gross weight: 1.69 g, yield: 67.6%. $^1$H NMR (400 MHz, DMSO) δ=12.16 (s, 2H), 10.66 (s, 1H), 8.90 (d, J=2.8 Hz, 1H), 7.78 (dd, J=6.0, 2.8 Hz, 1H), 7.66 (m, 1H), 7.49-7.33 (m, 1H), 4.29 (s, 2H), 2.88 (m, 1H), 2.74 (m, 1H), 2.68-2.51 (m, 3H), 1.67 (s, 1H), 1.41-1.12 (m, 2H), 0.85 (d, J=6.4 Hz, 6H). ESI-MS: [$C_{20}H_{23}BClFN_2O_9$—H], calculated value: 499.67, measured value: 498.98; [$C_{20}H_{23}BClFN_2O_9$+Na$^+$], calculated value: 523.11; measured value: 522.97.

Preparation Example 18

Preparation of Compound 6a: (R)-2,2'-(2-(1-(2-(2-chloro-5-bromo-benzoylamino)acetylamino)-3-methylbutyl)-5-oxo-1,3,2-dioxaborolan-4,4-diyl) diacetic acid Step 1: Preparation of Compound 3a: 2-chloro-5-bromo-N-[2-({(1R)-3-methyl-1-[(3aR,4R,6R,7aS)-3a,5,5-trimethylhexahydro-4,6-endo-methylene-1,3,2-benzodioxaborolan-2-yl]butyl}amino)-2-oxoethyl]benzamide

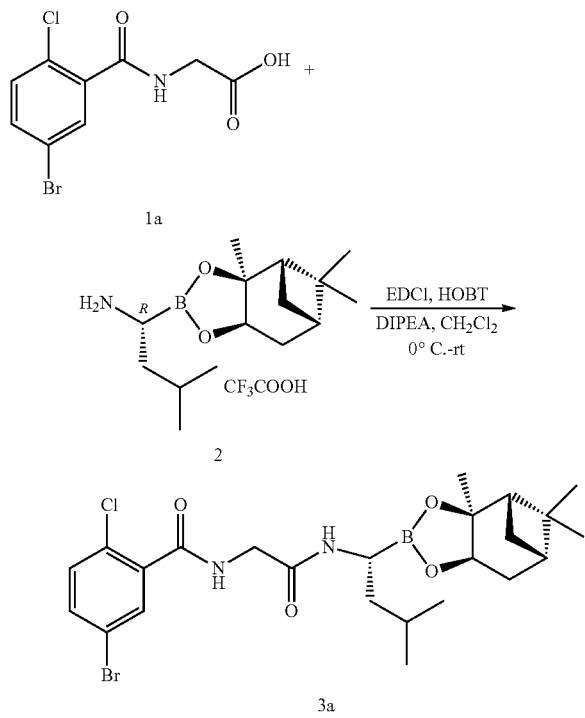

In a 20 L reactor, 990.0 g of [(2-chloro-5-bromobenzoyl)amino] acetic acid (compound 1a, 3.38 mol) was dissolved with 8.4 L of methylene chloride. The resultant mixture was stirred under ice bath condition for 10 min, 712.8 g of EDCI (3.72 mol, 1.10 eq.) and 502.9 g of HOBT(3.72 mol, 1.10 eq.) were added and stirred for 15 min, and then 1347.7 g of (R)-1-[(3aS,4S,6S,7aR)-3a,5,5-trimethylhexahydro-4,6-endo-methylene-1,3,2-benzodioxaborolan-2-yl]-3-methyl-1-butylamino-2,2,2-trifluoroacetate (compound 2, 3.55 mol, 1.05 eq.) was added and stirred under ice bath condition for 10 min. A mixture of 1471.9 mL of DIPEA (8.45 mol, 2.50 eq.) and 1.5 L of methylene chloride were dropwise added in about 1.5 h. After the dropping was finished, the reaction mixture was gradually warmed up to room temperature and reacted overnight. TLC was used to monitor the reaction until the raw material 1a was consumed completely. After the reaction was completed, the reaction mixture was successively washed with 5.0 L of water, 5.0 L of 3% $K_2CO_3$ solution, 5.0 L of 3% $H_3PO_4$ solution, 5.0 L of water and 5.0 L of 50% NaCl solution. The methylene chloride organic phase was collected, dried with 500 g of anhydrous sodium sulfate for 1 h, and concentrated in vacuum to very small volume. Then 5.0 L of n-heptane was added to the concentrated residual methylene chloride phase to produce a lot of white solid. The mixture was suction filtered and the filter cake was dried to obtain a white solid product, namely, compound (3a): 2-chloro-5-bromo-N-[2-({(1R)-3-methyl-1-[(3aR,4R,6R,7aS)-3a,5,5-trimethylhexahydro-4,6-endo-methylene-1,3,2-benzodioxaborolan-2-yl]butyl}amino)-2-oxoethyl]benzamide. Gross weight: 1510.0 g; yield: 82.8%. 1H NMR (400 MHz, DMSO) δ=9.11-8.87 (m, 2H), 7.77-7.64 (d, J=2.4 Hz, 1H), 7.64-7.61 (dd, J=8.8 Hz, 2.4 Hz, 1H), 7.46 (d, J=8.8 Hz, 1H), 4.18-3.92 (m, 2H), 2.22 (m, 1H), 2.11-2.00 (m, 1H), 1.90-1.64 (m, 4H), 1.43-1.18 (m, 10H), 0.94-0.70 (m, 10H).

Step 2: Preparation of Compound 4a: [(1R)-1-({[(2-chloro-5-bromo-benzoyl)amino]acetyl}amino)-3-methylbutyl]boric acid

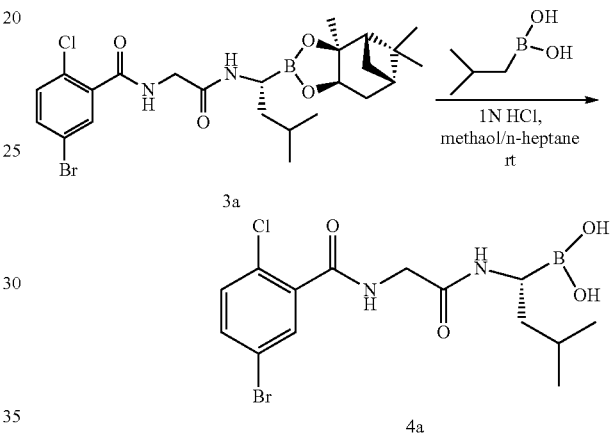

In a 20 L reactor, 1300.0 g (2.41 mol) of the compound 3a obtained as above was dissolved by adding 6.5 L of methanol under stirring. Then 6.5 L of n-heptane and 491.4 g of isobutyl boric acid (4.82 mol, 2.0 eq) were added under stirring at room temperature. After stirring for 15 min, 3.62 L (3.62 mol, 1.5 eq.) of 1N HCl solution dropwise added in about 1.5 h. After the dropping was finished, the reaction mixture was stirred violently at room temperature overnight, and TLC was used to monitor the reaction until the raw material 3a was consumed completely. After the reaction completed, the reaction mixture was left to stand and formed two phases. The methanol phase was washed twice with 2.6 L×2 n-heptane, then the methanol phase was collected and concentrated to ¼ volume. 2.6 L of methylene chloride and 1.0 L of water were added to the methanol phase under ice bath condition, and the resultant mixture was neutralized to alkalinity (pH was about 10) with 2N NaOH solution under stirring, extracted and separated. The aqueous phase was washed twice with 2.6 L×2 methylene chloride and collected. Then, under the condition of ice bath, 5.2 L of methylene chloride was added to the water phase, the resultant mixture was neutralized to weak acidity (pH was about 4) with 1N HCl solution, extracted and separated. The aqueous phase was washed twice with 2.6 L×2 methylene chloride, and the methylene chloride phases were combined, washed once with 2.6 L of 50% sodium chloride solution, dried with 1000 g of anhydrous sodium sulfate for 1 h, and then concentrated in vacuum to very small volume. Then, 6.0 L of n-heptane was added to the concentrated residual methylene chloride phase while stirring, and a lot of white solid was produced in the system. After suction filtration, the filter cake was dried to obtain white solid product, namely, compound (4a): [(1R)-1-({[(2-chloro-5-bromo-benzoyl)amino]acetyl}amino)-3-methylbutyl]boric acid. Gross weight: 752.0 g, yield: 77.0%. $^1$H NMR (400 MHz, DMSO) δ=9.03-8.93 (m, 1H), 8.75 (m, 1H), 7.83-7.76 (d, J=4.8, 1H), 7.67 (m, 1H), 7.49 (dd, J=8.8, 4.8 Hz, 1H), 4.05 (d, J=6.4 Hz, 2H), 2.71-2.64 (m, 1H), 1.63 (m, 1H), 1.45-1.22 (m, 2H), 0.85 (dd, J=6.4, 2.0 Hz, 6H). $^{13}$C NMR (101 MHz, DMSO) δ=171.85, 168.16, 165.65, 138.07, 134.19, 132.22, 130.08, 120.18, 55.37, 25.66, 23.43, 23.35, 22.57; melting point: 118-120° C.

Step 3: Preparation of Compound 6a: (R)-2,2'-(2-(1-(2-(2-chloro-5-bromo-benzoylamino)acetylamino)-3-methylbutyl)-5-oxo-1,3,2-dioxaborolan-4,4-diyl)diacetic acid

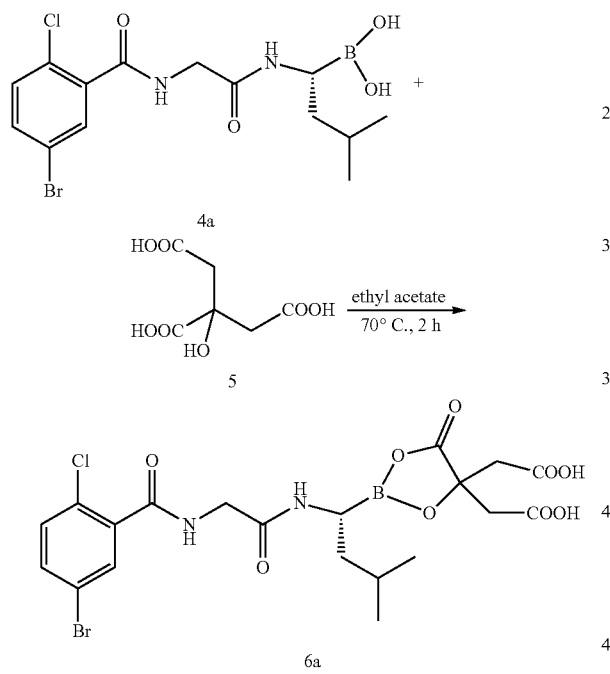

In a 250 mL round-bottom flask, 12.16 g (30 mmol) of compound 4a obtained as above was dissolved by adding 120 mL of ethyl acetate under stirring. The resultant mixture was warmed to 70° C. and 6.30 g of citric acid monohydrate (compound 5, 30 mmol, 1.0 eq.) was added thereto under stirring. After reacting for about 0.5 h, a white solid was produced in the system and the mixture was further reacted for 1 h under heating condition. The reaction mixture was cooled to room temperature, and subjected to suction filtration. The resultant white solid filter cake was washed twice with 15 mL×2 ethyl acetate, and suction-dried in an oil pump vacuum to obtain white solid product (6a): (R)-2,2'-(2-(1-(2-(2-chloro-5-bromo-benzoylamino)acetylamino)-3-methylbutyl)-5-oxo-1,3,2-dioxaborolan-4,4-diyl)diacetic acid. Gross weight: 14.0 g, yield: 83.1%. $^1$H NMR (400 MHz, DMSO) δ=12.16 (s, 2H), 10.71 (s, 1H), 9.17 (t, J=5.6 Hz, 1H), 7.82 (d, J=2.4 Hz, 1H), 7.68 (dd, J=8.4, 2.4 Hz, 1H), 7.48 (d, J=8.4 Hz, 1H), 4.32 (d, J=4.0 Hz, 2H), 2.72-2.87 (m, 5H), 1.68 (m, 1H), 1.02-1.26 (m, 2H), 0.87 (d, J=6.4 Hz, 6H). ESI-MS: [C$_{20}$H$_{23}$BBrClN$_2$O$_9$+Na$^+$], calculated value: 583.03, measured value: 583.10.

Preparation Example 19

Preparation of Compound 6c: (R)-2,2'-(2-(1-(2-(2-fluoro-5-trifluoromethyl-benzoylamino)acetylamino)-3-methylbutyl)-5-oxo-1,3,2-dioxaborolan-4,4-diyl)diacetic acid Step 1: Preparation of Compound 3c: 2-fluoro-5-trifluoromethyl-N-[2-({(1R)-3-methyl-1-[(3aR,4R,6R,7aS)-3a,5,5-trimethylhexahydro-4,6-endo-methylene-1,3,2-benzodioxaborolan-2-yl]butyl}amino)-2-oxoethyl]benzamide

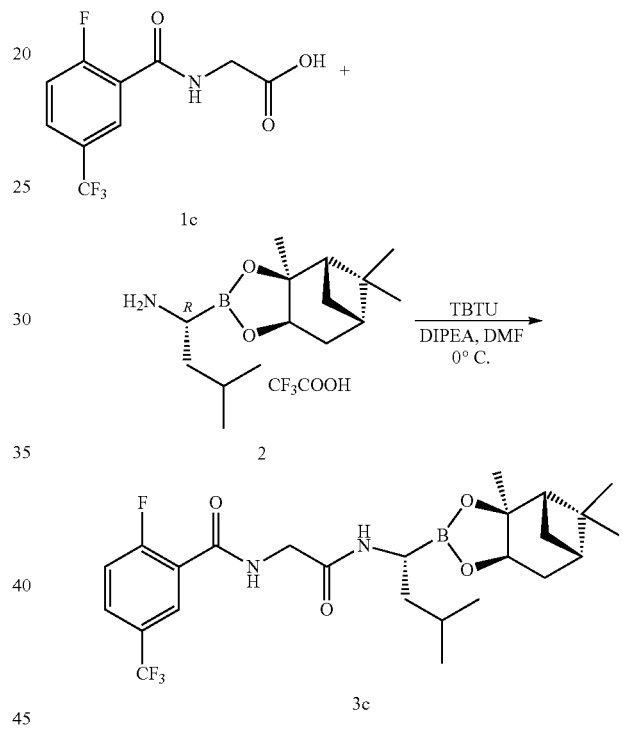

Into a 250 mL round-bottom flask, 10.60 g [(2-fluoro-5-trifluoromethyl-benzoyl) amino]acetic acid (compound 1c, 40.0 mmol) and 100 mL of DMF(N, N-dimethylformamide) were added. The resultant mixture was stirred under ice bath condition for 10 min, then 14.13 g of TBTU (44.0 mmol, 1.10 eq) was added and stirred for 15 min, and then 15.93 g of (R)-1-[(3aS,4S,6S,7aR)-3a,5,5-trimethylhexahydro-4,6-endo-methylene-1,3,2-benzodioxaborolan-2-yl]-3-methyl-1-butylamino-2,2,2-trifluoroacetate (compound 2, 42.0 mmol, 1.05 eq.) was added and stirred under ice bath condition for 10 min. A mixture of 19.16 mL of DIPEA (110.0 mmol, 2.50 eq.) and 20 mL of DMF were dropwise added in about 15 min. After the dropping was finished, the reaction mixture was gradually warmed up to room temperature and reacted for about 4 hr. TLC was used to monitor the reaction until the raw material 1c was consumed completely. After the reaction was completed, 150 mL of ethyl acetate was added into the reaction system to disperse the reaction mixture, and then 150 mL of water was added for extraction and liquid separation. The aqueous phase was reverse extracted once with 50 mL of ethyl acetate, and the ethyl acetate phases were combined and successively washed with 100 mL of 3% $K_2CO_3$ solution, 100 mL of 3% $H_3PO_4$ solution and 100 ml of 50% sodium chloride solution, and then the ethyl acetate organic phases were collected, dried with 50 g of anhydrous sodium sulfate for 1 h, and concentrated to dryness in vacuum to obtain a white solid product, namely, compound (3c): 2-fluoro-5-trifluoromethyl-N-[2-({(1R)-3-methyl-1-[(3aR,4R,6R,7aS)-3a,5,5-trimethylhexahydro-4,6-endo-methylene-1,3,2-benzodioxaborolan-2-yl]butyl}amino)-2-oxoethyl]benzamide. Gross weight: 18.0 g; yield: 87.8%.

Step 2: Preparation of Compound 4c: [(1R)-1-({[(2-fluoro-5-trifluoromethyl-benzoyl)amino]acetyl}amino)-3-methylbutyl]boric acid

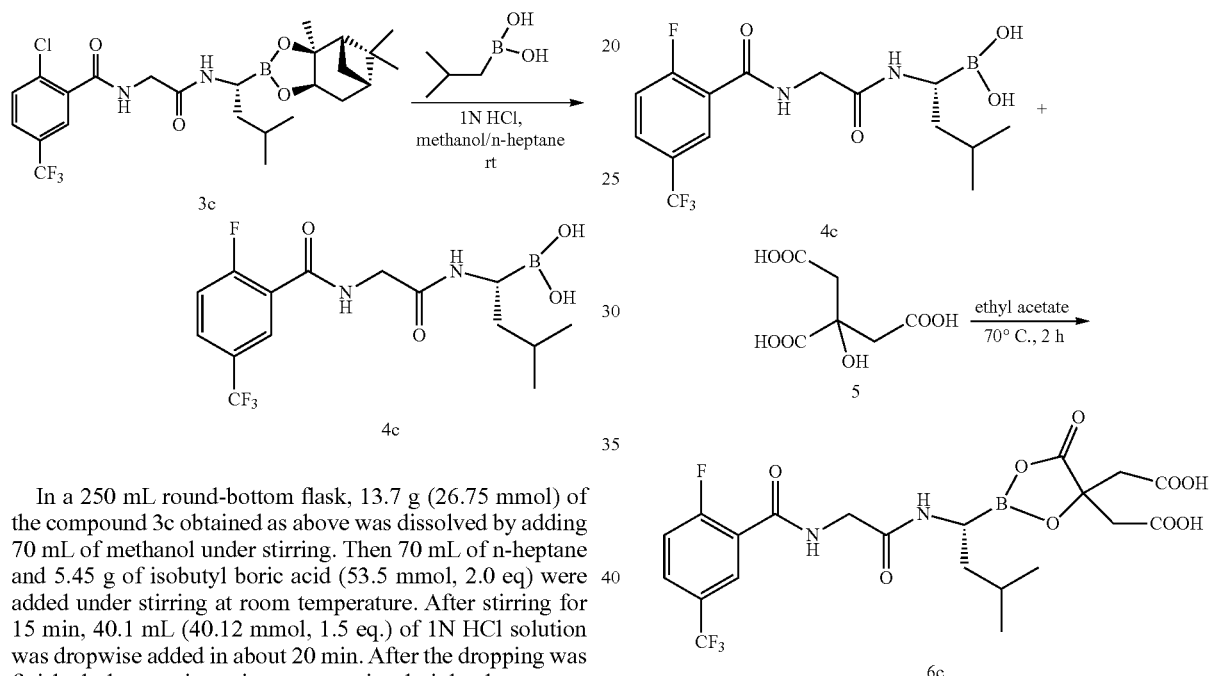

In a 250 mL round-bottom flask, 13.7 g (26.75 mmol) of the compound 3c obtained as above was dissolved by adding 70 mL of methanol under stirring. Then 70 mL of n-heptane and 5.45 g of isobutyl boric acid (53.5 mmol, 2.0 eq) were added under stirring at room temperature. After stirring for 15 min, 40.1 mL (40.12 mmol, 1.5 eq.) of 1N HCl solution was dropwise added in about 20 min. After the dropping was finished, the reaction mixture was stirred violently at room temperature overnight, and TLC was used to monitor the reaction until the raw material 3c was consumed completely. After the reaction was completed, the reaction mixture was left to stand and formed two phases. The methanol phase was washed twice with 50 mL×2 n-heptane, then the methanol phase was collected and concentrated to ¼ volume. 50 mL of methylene chloride and 50 mL of water were added to the methanol phase under ice bath condition, and the resultant mixture was neutralized to alkalinity (pH was about 10) with 2N NaOH solution under stirring, extracted and separated. The aqueous phase was washed twice with 50 mL×2 methylene chloride and collected. Under the condition of ice bath, 80 mL of methylene chloride was added to the water phase, the resultant mixture was neutralized to weak acidity (pH was about 4) with 1N HCl solution, extracted and separated. The aqueous phase was washed twice with 50 mL×2 methylene chloride, and the methylene chloride phases were combined, washed once with 100 mL of 50% sodium chloride solution, dried with 50 g of anhydrous sodium sulfate for 1 h, and then concentrated in vacuum to remain very small volume. Then, 60 mL of n-heptane was added to the concentrated residual methylene chloride phase while stirring, and a lot of white solid was produced in the system. After suction filtration, the filter cake was dried to obtain white solid product, namely, compound 4c: [(1R)-1-({[(2-fluoro-5-trifluoromethyl-benzoyl)amino]acetyl}amino)-3-methylbutyl]boric acid. Gross weight: 7.50 g, yield: 74.1%. $^1$H NMR (400 MHz, DMSO) δ=9.03 (s, 1H), 8.75 (s, 1H), 7.83-7.76 (d, J=4.8, 1H), 7.87 (m, 1H), 7.79 (m, 1H), 4.05 (d, J=6.4 Hz, 2H), 2.71-2.64 (m, 1H), 1.63 (m, 1H), 1.48 (m, 2H), 0.85 (d, J=6.4, 6H). ESI-MS: [$C_{15}H_{19}BF_4N_2O_4$—H], calculated value: 377.14; measured value: 377.14.

Step 3: Preparation of Compound 6c: (R)-2,2'-(2-(1-(2-(2-fluoro-5-trifluoromethyl-benzoylamino)acetylamino)-3-methylbutyl)-5-oxo-1,3,2-dioxaborolan-4,4-diyl)diacetic acid In a 100 mL round-bottom flask, 1.51 g (4.0 mmol) of compound 4c was dissolved by adding 20 mL of ethyl acetate under stirring. The resultant mixture was warmed to 70° C. and 0.84 g of citric acid monohydrate (compound 5, 4.0 mmol, 1.0 eq.) was added thereto under stirring. After reacting for about 0.5 h, a white solid was produced in the system and the mixture was further reacted for 1 h under heating condition. The reaction mixture was cooled to room temperature, and subjected to suction filtration. The resultant white solid filter cake was washed twice with 15 mL×2 ethyl acetate, and suction-dried in an oil pump vacuum to obtain white solid product (6c): (R)-2,2'-(2-(1-(2-(2-fluoro-5-trifluoromethyl-benzoylamino)acetylamino)-3-methylbutyl)-5-oxo-1,3,2-dioxaborolan-4,4-diyl)diacetic acid. Gross weight: 1.75 g, yield: 82.0%. $^1$H NMR (400 MHz, DMSO) δ=12.12 (s, 2H), 10.64 (s, 1H), 8.88 (m, 1H), 7.61 (m, 1H), 7.47 (m, 1H), 7.34 (m, 1H), 4.42-4.18 (m, 2H), 2.89 (m, 1H), 2.82-2.51 (m, 4H), 1.68 (m, 1H), 1.24-1.08 (m, 2H), 0.86 (d, J=6.4 Hz, 6H). ESI-MS: [$C_{21}H_{23}BF_4N_2O_9$—H], calculated value: 533.23, measured value: 532.99; [$C_{21}H_{23}BF_4N_2O_9$+Na$^+$], calculated value: 557.13; measured value: 557.03.

Preparation Example 20

Preparation of Compound 6r: (R)-2,2'-(2-(1-(2-(2-fluoro-5-methyl-benzoylamino)acetylamino)-3-methylbutyl)-5-oxo-1,3,2-dioxaborolan-4,4-diyl) diacetic acid

Step 1: Preparation of Compound 3r: 2-fluoro-5-methyl-N-[2-({(1R)-3-methyl-1-[(3aR,4R,6R,7aS)-3a,5,5-trimethylhexahydro-4,6-endo-methylene-1,3,2-benzodioxaborolan-2-yl]butyl}amino)-2-oxoethyl]benzamide

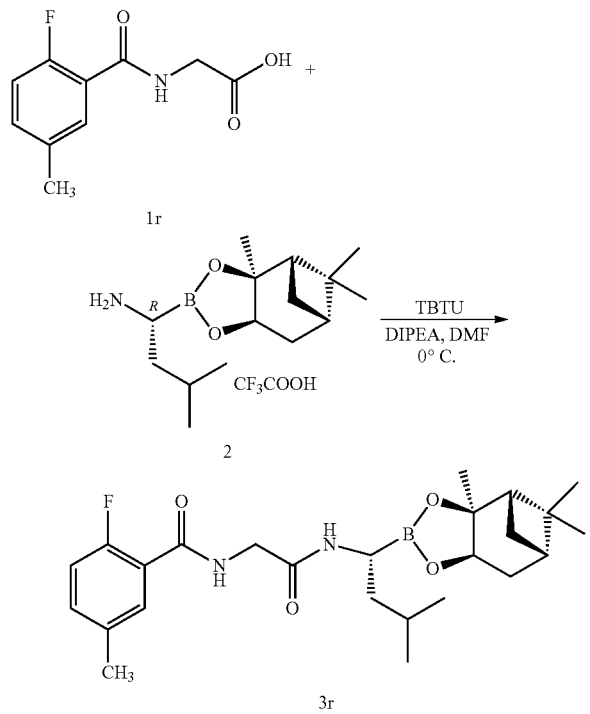

Into a 100 mL round-bottom flask, 5.28 g [(2-fluoro-5-methyl-benzoyl) amino] acetic acid (compound 1r, 25.0 mmol) and 29 mL of DMF (N, N-dimethylformamide) were added. The resultant mixture was stirred under ice bath condition for 10 min, then 9.63 g of TBTU (30.0 mmol, 1.20 eq) was added and stirred for 15 min, and then 9.95 g of (R)-1-[(3aS,4S,6S,7aR)-3a,5,5-trimethylhexahydro-4,6-endo-methylene-1,3,2-benzodioxaborolan-2-yl]-3-methyl-1-butylamino-2,2,2-trifluoroacetate (compound 2, 26.25 mmol, 1.05 eq.) was added and stirred under ice bath condition for 10 min. 10.89 mL of DIPEA (62.50 mmol, 2.50 eq.) was dropwise added in about 15 min. After the dropping was finished, the reaction mixture was gradually warmed up to room temperature and reacted for about 4 hr. TLC was used to monitor the reaction until the raw material 1r was consumed completely. After the reaction was completed, 60 mL of ethyl acetate was added into the reaction system to disperse the reaction mixture, and then 40 mL of water was added for extraction and liquid separation. The aqueous phase was reverse extracted once with 50 mL of ethyl acetate, and the ethyl acetate phases were combined. The resultant ethyl acetate phase was successively washed with 80 mL of 3% $K_2CO_3$ solution, 80 mL of 3% $H_3PO_4$ solution and 80 ml of 50% sodium chloride solution, and then the ethyl acetate organic phases were collected, dried with 50 g of anhydrous sodium sulfate for 1 h, and concentrated to dryness in vacuum to obtain a white solid product, namely, compound (3r): 2-fluoro-5-methyl-N-[2-({(1R)-3-methyl-1-[(3aR,4R,6R,7aS)-3a,5,5-trimethylhexahydro-4,6-endo-methylene-1,3,2-benzodioxaborolan-2-yl]butyl}amino)-2-oxoethyl]benzamide, which was directly used in the next reaction without purification.

Step 2: Preparation of Compound 4f: [(1R)-1-({[(2-fluoro-5-methyl-benzoyl)amino]acetyl}amino)-3-methylbutyl]boric acid

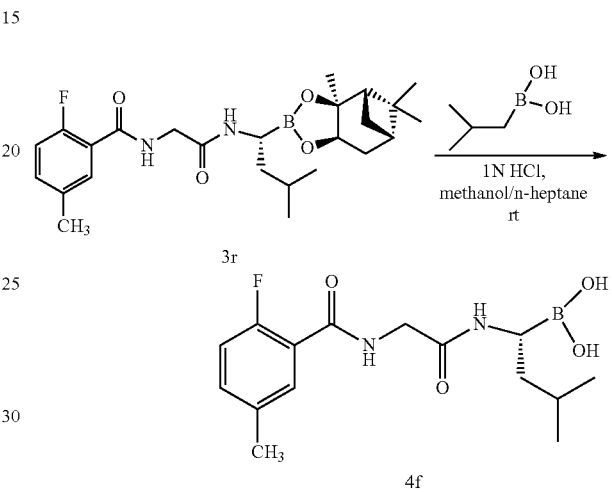

In a 250 mL round-bottom flask, the crude product of compound 3r obtained as above was dissolved by adding 58 mL of methanol under stirring. Then 48 mL of n-heptane and 3.82 g of isobutyl boric acid (37.50 mmol, 1.5 eq) were added under stirring at room temperature. After stirring for 15 min, 37.50 mL (37.50 mmol, 1.5 eq.) of 1N HCl solution was dropwise added in about 15 min. After the dropping was finished, the reaction mixture was stirred violently at room temperature overnight, and TLC was used to monitor the reaction until the raw material 3r was consumed completely. After the reaction was completed, the reaction mixture was left to stand and formed two phases. The methanol phase was washed twice with 50 mL×2 n-heptane, then the methanol phase was collected and concentrated to ¼ volume. 50 mL of methylene chloride and 50 mL of water were added to the methanol phase under ice bath condition, and the resultant mixture was neutralized to alkalinity (pH was about 10) with 2N NaOH solution under stirring, extracted and separated. The aqueous phase was washed twice with 50 mL×2 methylene chloride and collected. Under the condition of ice bath, 80 mL of methylene chloride was added to the water phase, the resultant mixture was neutralized to weak acidity (pH was about 4) with 1N HCl solution, extracted and separated. The aqueous phase was washed twice with 50 mL×2 methylene chloride, and the methylene chloride phases were combined, washed once with 100 mL of 50% sodium chloride solution, dried with 50 g of anhydrous sodium sulfate for 1 h, and then concentrated in vacuum to remain very small volume. Then, 60 mL of n-heptane was added to the concentrated residual methylene chloride phase while stirring, and a lot of white solid was produced in the system. After suction filtration, the filter cake was dried to obtain white solid product, namely, compound (4f): [(1R)-1-({[(2-fluoro-5-methyl-benzoyl)amino]acetyl}amino)-3-methylbutyl]boric acid. Gross weight: 5.95 g, yield: 73.5%.

Step 3: Preparation of Compound 6r: (R)-2,2'-(2-(1-(2-(2-fluoro-5-methyl-benzoylamino)acetylamino)-3-methylbutyl)-5-oxo-1,3,2-dioxaborolan-4,4-diyl)diacetic acid

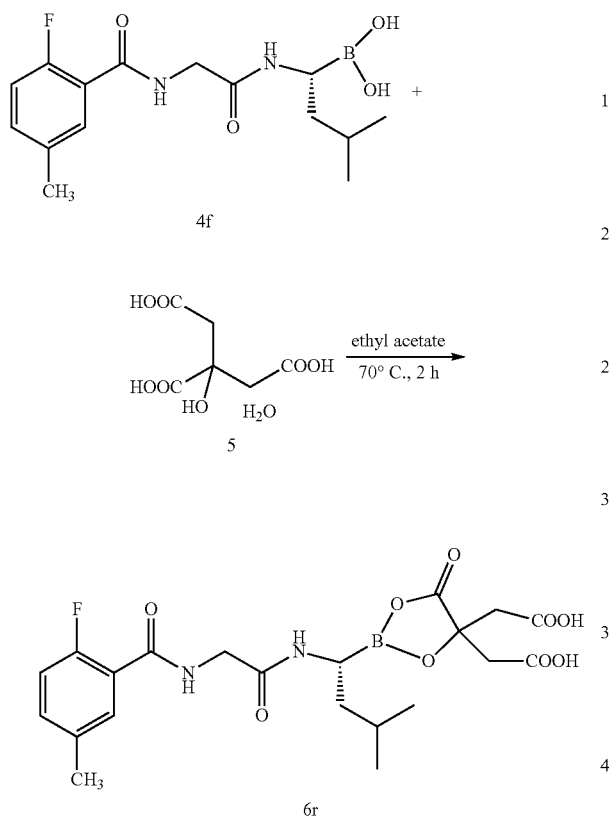

In a 100 mL round-bottom flask, 1.62 g (5.0 mmol) of compound 4f was dissolved by adding 35 mL of ethyl acetate under stirring. The resultant mixture was warmed to 70° C. and 1.07 g of citric acid monohydrate (compound 5, 5.10 mmol, 1.02 eq.) was added thereto under stirring. After reacting for about 5 min, a white solid was produced in the system and the mixture was further reacted for 2 h under heating condition. The reaction mixture was cooled to room temperature, and subjected to suction filtration. The resultant white solid filter cake was washed twice with 15 mL×2 ethyl acetate, and suction-dried in an oil pump vacuum to obtain white solid product (6r): (R)-2,2'-(2-(1-(2-(2-fluoro-5-methyl-benzoylamino)acetylamino)-3-methylbutyl)-5-oxo-1,3,2-dioxaborolan-4,4-diyl)diacetic acid. Gross weight: 2.15 g, yield: 89.5%. $^1$H NMR (400 MHz, DMSO) δ=11.98 (s, 2H), 10.66 (s, 1H), 8.67 (dd, J=9.7, 5.3 Hz, 1H), 7.64-7.49 (m, 1H), 7.45-7.30 (m, 1H), 7.19 (m, 1H), 4.27 (d, J=4.4 Hz, 2H), 2.89 (d, J=14.2 Hz, 1H), 2.75 (m, 1H), 2.56 (m, 3H), 2.32 (s, 3H), 1.67 (s, 1H), 1.42-1.04 (m, 2H), 0.85 (d, J=6.4 Hz, 6H). ESI-MS: [$C_{21}H_{26}BFN_2O_9$—H], calculated value: 479.25, measured value: 479.47; [$C_{21}H_{26}BFN_2O_9$+Na$^+$], calculated value: 503.24; measured value: 502.99.

Preparation Example 21

Preparation of Compound 6s: (R)-2,2'-(2-(1-(2-(2-fluoro-5-fluoro-benzoylamino)acetylamino)-3-methylbutyl)-5-oxo-1,3,2-dioxaborolan-4,4-diyl)diacetic acid Step 1: Preparation of Compound 3s: 2-fluoro-5-fluoro-N-[2-({(1R)-3-methyl-1-[(3aR,4R,6R,7aS)-3a,5,5-trimethylhexahydro-4,6-endo-methylene-1,3,2-benzodioxaborolan-2-yl]butyl}amino)-2-oxoethyl]benzamide

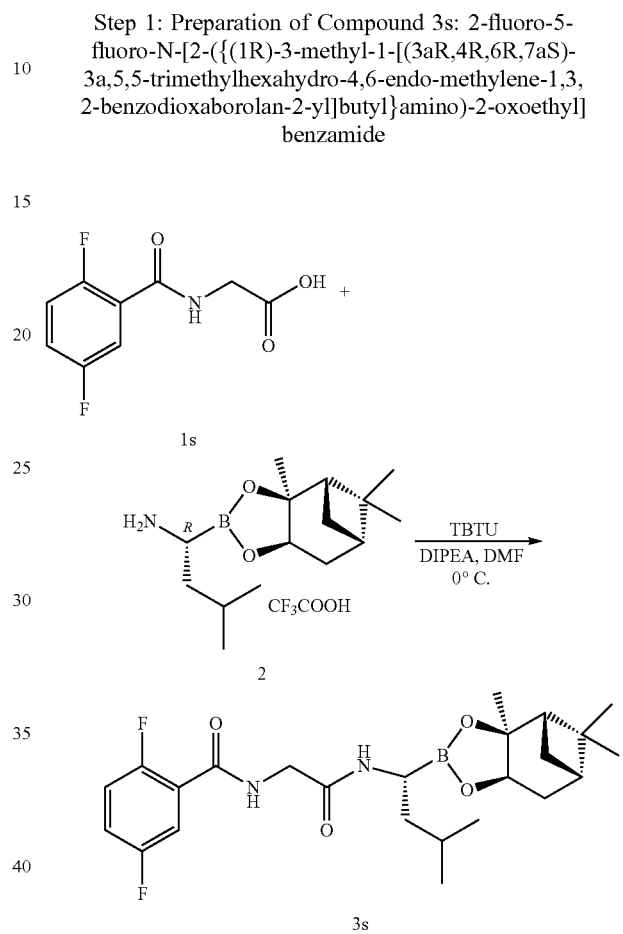

Into a 100 mL round-bottom flask, 5.38 g [(2-fluoro-5-fluoro-benzoyl) amino] acetic acid (compound is, 25.0 mmol) and 29 mL of DMF (N, N-dimethylformamide) were added. The resultant mixture was stirred under ice bath condition for 10 min, then 9.63 g of TBTU (30.0 mmol, 1.20 eq) was added and stirred for 15 min, and then 9.95 g of (R)-1-[(3aS,4S,6S,7aR)-3a,5,5-trimethylhexahydro-4,6-endo-methylene-1,3,2-benzodioxaborolan-2-yl]-3-methyl-1-butylamino-2,2,2-trifluoroacetate (compound 2, 26.25 mmol, 1.05 eq.) was added and stirred under ice bath condition for 10 min. 10.89 mL of DIPEA (62.50 mmol, 2.50 eq.) was dropwise added in about 15 min. After the dropping was finished, the reaction mixture was gradually warmed up to room temperature and reacted for about 4 hr. TLC was used to monitor the reaction until the raw material is was consumed completely. After the reaction was completed, 60 mL of ethyl acetate was added into the reaction system to dispersed the reaction mixture, and then 40 mL of water was added for extraction and liquid separation. The aqueous phase was reverse extracted once with 50 mL of ethyl acetate, and the ethyl acetate phases were combined. The resultant ethyl acetate phase was successively washed with 80 mL of 3% $K_2CO_3$ solution, 80 mL of 3% $H_3PO_4$ solution and 80 ml of 50% sodium chloride solution, and then the ethyl acetate organic phases were collected, dried with 50 g of anhydrous sodium sulfate for 1 h, and concentrated to dryness in vacuum to obtain a white solid product, namely, compound (3s): 2-fluoro-5-fluoro-N-[2-({(1R)-3-methyl-1-[(3aR,4R,6R,7aS)-3a,5,5-trimethylhexahydro-4,6-endo-methylene-1,3,2-benzodioxaborolan-2-yl]butyl}amino)-2-oxoethyl]benzamide, which was directly used in the next reaction without purification.

Step 2: Preparation of Compound 4g: [(1R)-1-({[(2-fluoro-5-methyl-benzoyl)amino]acetyl}amino)-3-methylbutyl]boric acid

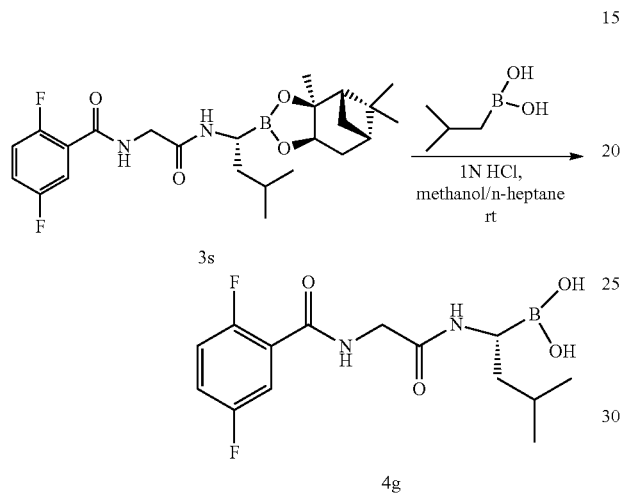

In a 250 mL round-bottom flask, the crude product of compound 3s obtained as above was dissolved by adding 58 mL of methanol under stirring. Then 48 mL of n-heptane and 3.82 g of isobutyl boric acid (37.50 mmol, 1.5 eq) were added under stirring at room temperature. After stirring for 15 min, 37.50 mL (37.50 mmol, 1.5 eq.) of 1N HCl solution was dropwise added in about 15 min. After the dropping was finished, the reaction mixture was stirred violently at room temperature overnight, and TLC was used to monitor the reaction until the raw material 3s was consumed completely. After the reaction was completed, the reaction mixture was left to stand and formed two phases. The methanol phase was washed twice with 50 mL×2 n-heptane, then the methanol phase was collected and concentrated to ¼ volume. 50 mL of methylene chloride and 50 mL of water were added to the methanol phase under ice bath condition, and the resultant mixture was neutralized to alkalinity (pH was about 10) with 2N NaOH solution under stirring, extracted and separated. The aqueous phase was washed twice with 50 mL×2 methylene chloride and collected. Under the condition of ice bath, 80 mL of methylene chloride was added to the water phase, the resultant mixture was neutralized to weak acidity (pH was about 4) with 1N HCl solution, extracted and separated. The aqueous phase was washed twice with 50 mL×2 methylene chloride, and the methylene chloride phases were combined, washed once with 100 mL of 50% sodium chloride solution, dried with 50 g of anhydrous sodium sulfate for 1 h, and then concentrated in vacuum to remain very small volume. Then, 60 mL of n-heptane was added to the concentrated residual methylene chloride phase while stirring, and a lot of white solid was produced in the system. After suction filtration, the filter cake was dried to obtain white solid product, namely, compound (4g): [(1R)-1-({[(2-fluoro-5-fluoro-benzoyl)amino]acetyl}amino)-3-methylbutyl]boric acid. Gross weight: 5.48 g, yield: 66.8%.

Step 3: Preparation of Compound 6s: (R)-2,2'-(2-(1-(2-(2-fluoro-5-fluoro-benzoylamino)acetylamino)-3-methylbutyl)-5-oxo-1,3,2-dioxaborolan-4,4-diyl)diacetic acid

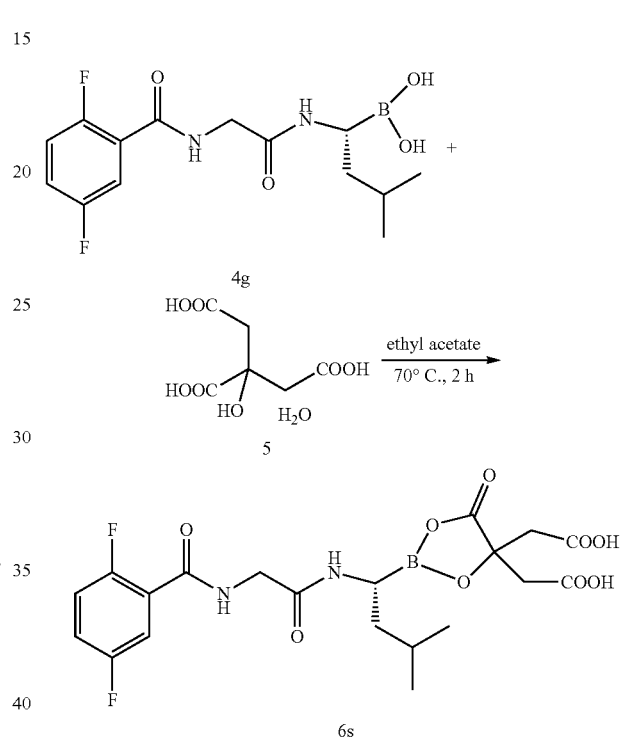

In a 100 mL round-bottom flask, 1.64 g (5.0 mmol) of compound 4f was dissolved by adding 35 mL of ethyl acetate under stirring. The resultant mixture was warmed to 70° C. and 1.07 g of citric acid monohydrate (compound 5, 5.10 mmol, 1.02 eq.) was added thereto under stirring. After reacting for about 10 min, a white solid was produced in the system and the mixture was further reacted for 2 h under heating condition. The reaction mixture was cooled to room temperature, and subjected to suction filtration. The resultant white solid filter cake was washed twice with 15 mL×2 ethyl acetate, and suction-dried in an oil pump vacuum to obtain white solid product (6s): (R)-2,2'-(2-(1-(2-(2-fluoro-5-fluoro-benzoylamino)acetylamino)-3-methylbutyl)-5-oxo-1,3,2-dioxaborolan-4,4-diyl)diacetic acid. Gross weight: 1.95 g, yield: 80.5%. $^1$H NMR (400 MHz, DMSO) δ=12.12 (s, 2H), 10.73 (s, 1H), 8.87 (d, J=3.2 Hz, 1H), 7.56 (m, 1H), 7.50-7.23 (m, 2H), 4.30 (s, 2H), 3.02-2.69 (m, 2H), 2.56 (m, 3H), 1.68 (m, 1H), 1.46-1.04 (m, 2H), 0.85 (d, J=5.6 Hz, 6H). ESI-MS: [$C_{20}H_{23}BF_2N_2O_9$—H], calculated value: 483.22, measured value: 483.50; [$C_{20}H_{23}BF_2N_2O_9$+Na$^+$], calculated value: 507.22; measured value: 507.03.

Activity Experiment Example 1: Activity Test on Human Multiple Myeloma Cells RPMI-8226 and Human Multiple Myeloma Cells MM.1S Cells RPMI-8226 (human multiple myeloma cells from ATCC (American type culture collection), ATCC CCL-155) and cells MM.1S (human multiple myeloma cells from ATCC (American type culture collection), ATCC CRL-2974) were cultured to logarithmic growth phase in RPMI 1640 medium containing 10% fetal bovine serum at 37° C. and 5% $CO_2$. The cells were inoculated into 96-well culture plates in proper quantity per well. After culturing at 37° C. and 5% $CO_2$ for 24 h, solvent control DMSO or test compounds dissolved in DMSO were added to the wells, wherein the starting concentration of the test compounds were 0.3 M, and diluted 3-fold each time for a total of 6 times to obtain 6 concentration gradients. The cells were incubated together with the test compounds at 37° C. and 5% $CO_2$ for 48 h. CCK-8 reagent was added to each well and the cells were incubated at 37° C. for 2 h according to the reagent instructions, and the optical density value of each well was read with spectrophotometer at 450 nm wavelength.

The optical density value of the cells was set as Tz value when the drugs had null action on the cell, which represented the cell value when the drugs were added. The optical density values of the cells were set as C value after the cells were acted by solvent control DMSO for 48 h; and the optical density values of the cell were set as Ti value after the cells were acted by the test compounds for 48 h. According to the method proposed by NIH—NCI in the United States, the cells' response to drugs was calculated as follows: [(Ti−Tz)/(C−Tz)]×100 when Ti≥Tz; [(Ti−Tz)/Tz]×100 when Ti<Tz. According to the above calculation, the GI50 value (the concentration of the test compound required when the cell growth inhibition rate was 50%) was calculated by using the 4-parameter logistic model in XLfit software. Activity data were shown in table 1 below:

TABLE 1

| Compound | RPMI 8226 cells GI50(μM) value | MM.1S cells GI50(μM) value |
| --- | --- | --- |
| 6a | 0.010674 | 0.013313 |
| 6b | 0.012021 | 0.011212 |
| 6c | 0.018229 | 0.025983 |

TABLE 1-continued

| Compound | RPMI 8226 cells GI50(μM) value | MM.1S cells GI50(μM) value |
|---|---|---|
| MLN9708 | 0.012235 | 0.012773 |
| 61 | 0.013412 | 0.012047 |

Activity Experiment Example 2: Activity Test on Transplantation Tumor Model of Human Multiple Myeloma Cells MM.1S in CB17-SCID Mouse The model used in this experiment was the transplantation tumor model of human multiple myeloma cells line MM.1 S in CB17-SCID mouse (purchased from Beijing Weitong Lihua Experimental Animal Technology Co., Ltd.). Cryopreserved MM.1S cells were cultured in vitro by conventionally way after resuscitation. The cells were collected in logarithmic growth phase and diluted with serum-free culture medium or PBS to form a tumor cell suspension with a concentration of $5\times10^7$/ml. The tumor cell suspensions prepared above were taken with a 1 ml syringe and injected subcutaneously into the left armpit backrest side of the mouse, and 0.2 ml was injected into each inoculation site. About 1 to 2 weeks after the cultured tumor cells were injected into CB17-SCID mouse, the tumors were touched under the armpit. When the tumor volume was more than 100 mm$^3$, the tumor volume was measured and calculated, and the mice were randomly divided into groups according to the tumor volume.

The administration doses of different test samples were equivalent doses on a molar basis with a specific dose of 0.00831 mmol/kg.

Administration mode and frequency: The test samples were administered by oral gavage with a volume of 10 ml/kg. The model group was given equal volume of solvent. The test samples were administered twice a week for five times (with administration dose of 0.00831 mmol/kg, i.e., the dose of MLN9708 being 4.30 mg/kg, the dose of the compound 6a being 4.67 mg/kg, and the dose of the compound 6b being 4.53 mg/kg) for a duration of 19 days. The administration was conducted on the 1st, 4th, 8th, 11th and 15th day, and the experiment was finished on the 19th day.

The mental state, activity, eating and other general conditions of mice were observed every day, and the weight was measured twice a week. The short diameter (a) and long diameter (b) of each mouse tumor were measured with vernier caliper twice a week, and the tumor volume was calculated according to formula $(a^2 \times b)/2$. The relative tumor volume (RTV) was calculated according to the measured tumor volume, RTV=$V_t/V_0$. Wherein, $V_0$ was the tumor volume when random grouping (i.e. $d_0$) and $V_t$ was the tumor volume at each measurement (i.e. $d_n$). According to the following formula, evaluation index of anti-tumor activity, the relative tumor proliferation rate T/C (%), was calculated:

$$T/C\% = \frac{T_{RTV}}{C_{RTV}} \times 100\%$$

Note: $T_{RTV}$ is RTV of treatment group, and $C_{RTV}$ is RTV of model control group. Efficacy evaluation standard is T/C %≤40%, and after statistics procession, p<0.05 is considered significant.

On the 19th day, after the tumor was weighted and measured, the mice in each group were killed, and the tumor was dissected and weighed.

According to the tumor weight, the tumor inhibition rate (TGI) was calculated, TGI=((average tumor weight of model group−average tumor weight of administration group)/average tumor weight of model group)×100%.

The effects of each test sample on the tumor of the transplantation tumor model of human multiple myeloma MM.1S in SCID mouse were shown in tables 2 and 3 as well as FIG. 1.

TABLE 2

Relative tumor proliferation rate T/C(%) of proteasome inhibitor against transplantation tumor model of human multiple myeloma MM.1S in SCID mouse (T/C(%) = $T_{RTV}/C_{RTV}$, $T_{RTV}$ is average relative tumor volume of the administration group, $C_{RTV}$ is the average relative tumor volume of the model control group in the same period)

| group | Time | | | | |
|---|---|---|---|---|---|
| | day 4 T/C(%) | day 8 T/C(%) | day 11 T/C(%) | day 15 T/C(%) | day 19 T/C(%) |
| MLN9708 | 84.97 | 59.75 | 51.05 | 41.67 | 56.1 |
| 6a | 87.94 | 69.95 | 88.41▲ | 94.56▲ | 80.45 |
| 6b | 48.84▲ | 4.3▲▲ | 1.75▲▲ | 1.12▲▲ | 0.5▲▲ |

Note:
▲p < 0.05 when compared with the RTV original data of MLN9708 group in the same period,
▲▲p < 0.01
(RTV original data refers to the RTV value calculated by the measured value of tumor tissue volume of each experimental animal)

TABLE 3

Tumor weight ($\overline{X} \pm SD$, g) and tumor inhibition rate of proteasome inhibitor against the transplantation tumor model of human multiple myeloma MM.1S in SCID mouse

| group | tumor weight (g) | tumor inhibition rate (%) |
|---|---|---|
| model | 3.614 ± 0.855▲▲ | — |
| MLN9708 | 1.782 ± 1.361★★▲▲ | 50.69 |
| 6a | 2.471 ± 0.598★★▲▲ | 31.63 |
| 6b | 0.063 ± 0.072★★ | 98.26 |

Note:
★when compared with model group, p < 0.05;
★★when compared with model group, p < 0.01
▲when compared with 6b group, p < 0.05,
▲▲when compared with 6b group, P < 0.01;

The above experimental results show that the compound 6b can significantly inhibit tumor growth of transplantation tumor of human multiple myeloma MM.1S in SCID mouse at a low dose of 0.00831 mmol/kg. The compound 6b has a significantly stronger inhibitory effect on tumor growth than MLN9708(p<0.01) and the compound 6a(p<0.01), and the difference is statistically significant.

In addition, through the activity test on the transplantation tumor model in CB17-SCID mouse with the same method and procedure, the experimental data shows that the compound 6b has a significantly stronger inhibitory effect on tumor growth of the transplantation tumor of human multiple myeloma MM.1S in SCID mouse than that of the compound 6c, and the difference is statistically significant.

Activity Experiment Example 3: Activity Test on Human Multiple Myeloma Cells KMS-11

Cells KMS-11 (human multiple myeloma cells from JCRB ((Japanese Collection of Research Bioresources Cell Bank), AJCRB1179) were cultured to logarithmic growth phase in RPMI 1640 medium containing 10% fetal bovine serum at 37° C. and 5% $CO_2$. The cells were inoculated into a 96-well culture plate in proper quantity per well. After being cultured at 37° C. and 5% $CO_2$ for 24 h, solvent control DMSO or test compounds dissolved in DMSO were added to the cells, wherein the starting concentration of the test compound was 0.3 μM, and diluted 3-fold each time for a total of 6 times to obtain 6 concentration gradients. The cells were incubated with the test compounds at 37° C. and 5% $CO_2$ for 48 h. CCK-8 reagent was added to each well and the cells were incubated at 37° C. for 2 h according to the reagent instructions, and the optical density value of each well was read with spectrophotometer at 450 nm wavelength.

The optical density value of the cell was set as Tz value when the drug had null action on the cell, which represented the cell value when the drug was added. The optical density value of the cells was set as C value after the cells were acted by solvent control DMSO for 48 h; and the optical density value of the cell was set as Ti value after the cells were acted by the test compounds for 48 h. According to the method proposed by NIH—NCI in the United States, the cell response to drugs was calculated as follows: [(Ti−Tz)/(C−Tz)]×100 when Ti≥Tz; [(Ti−Tz)/Tz]×100 when Ti<Tz. According to the above calculation, the GI50 value (the concentration of the test compound as required when the cell growth inhibition rate was 500%) was calculated by using the 4-parameter logistic model in XLfit software. Activity data were shown in table 4 below:

TABLE 4

| Compound | KMS-11 cells: GI50 value (nM) |
|---|---|
| 4b | 35.69 |
| 6b | 39.72 |
| 6c | 57.83 |
| 6e | 34.06 |

TABLE 4-continued

| Compound | KMS-11 cells: GI50 value (nM) |
|---|---|
| 6f | 29.88 |
| 6l | 35.69 |
| 6q | 58.98 |
| 6r | 90.45 |
| 6s | 87.76 |

Activity Experiment Example 4: Activity Test on Transplantation Tumor Model of Human Multiple Myeloma Cells MM.1S in CB17-SCID Mouse The model used in this experiment was the transplantation tumor model of human multiple myeloma cells line MM.1S in CB17-SCID mouse. Cryopreserved MM.1S cells were cultured in vitro conventionally after resuscitation. The cells were collected in logarithmic growth phase and diluted with serum-free culture medium or PBS to form a tumor cell suspension with a concentration of $5 \times 10^7$/ml. The tumor cell suspensions prepared above were taken with a 1 ml syringe and injected subcutaneously into the left armpit backrest side of the mouse, and 0.2 ml was injected into each inoculation site. About 1 to 2 weeks after the cultured tumor cells were injected into the CB17-SCID mouse, the tumors were touched under the armpit. When the tumor volume was more than 100 mm³, the tumor volume was measured and calculated, and the mice were randomly divided into groups according to the tumor volume.

The administration doses of different test samples were equivalent doses on a molar basis with a specific dose of 0.00554 mmol/kg.

A dose of 0.00831 mmol/kg was once used in the same animal experimental model. In this experiment, the activity of each compound was further tested with a low dose. In the clinical use of MLN9708 (i.e. NINLARO®), due to the side effects of the drug, it is necessary to reduce the dose or stop the administration according to the instructions. Compounds with high titer can be administered at a lower dose, which is helpful to improve tolerance and reduce side reactions.

Administration mode and frequency: the test samples were administered by oral gavage with a volume of 10 ml/kg. The model group was given equal volume of solvent. The test samples were administered twice a week for five times with an administration dose of 0.00554 mmol/kg, i.e., the dose of MLN9708 being 2.86 mg/kg, the dose of the compound 6q being 2.77 mg/kg, the dose of the compound 6f being 2.80 mg/kg, and the dose of the compound 6b being 3.02 mg/kg, for a duration of 17 days. The administration was conducted on the 1st, 5th, 8th, 12th and 15th day, and the experiment was finished on the 17th day.

The mental state, activity, eating and other general conditions of mice were observed every day, and the weight was measured twice a week. The short diameter (a) and long diameter (b) of each mouse tumor were measured with a vernier caliper twice a week, and the tumor volume was calculated according to formula $(a^2 \times b)/2$. The relative tumor volume (RTV) was calculated according to the measured tumor volume, $RTV=V_t/V_0$. Wherein, $V_0$ was the tumor volume when random grouping (i.e. $d_0$) and $V_t$ was the tumor volume at each measurement (i.e. $d_0$). According to the following formula, evaluation index of anti-tumor activity relative to the relative tumor proliferation rate T/C (%) was calculated:

$$T/C\% = \frac{T_{RTV}}{C_{RTV}} \times 100\%$$

Note: $T_{RTV}$ is RTV of treatment group, and $C_{RTV}$ is RTV of model control group. According to "Technical Guidelines for Non-clinical Research of Cytotoxic Antitumor Drugs" issued by State Food and Drug Administration in China, the evaluation standard is T/C %≤40%, and after statistics procession, $p<0.05$ is considered significant.

On the 19th day, after the tumor was weighted and measured, the mice in each group were killed, and the tumor was dissected and weighed.

According to the tumor weight, the tumor inhibition rate (TGI) was calculated, TGI=((average tumor weight of model group−average tumor weight of administration group)/average tumor weight of model group)×100%.

Figure 2:
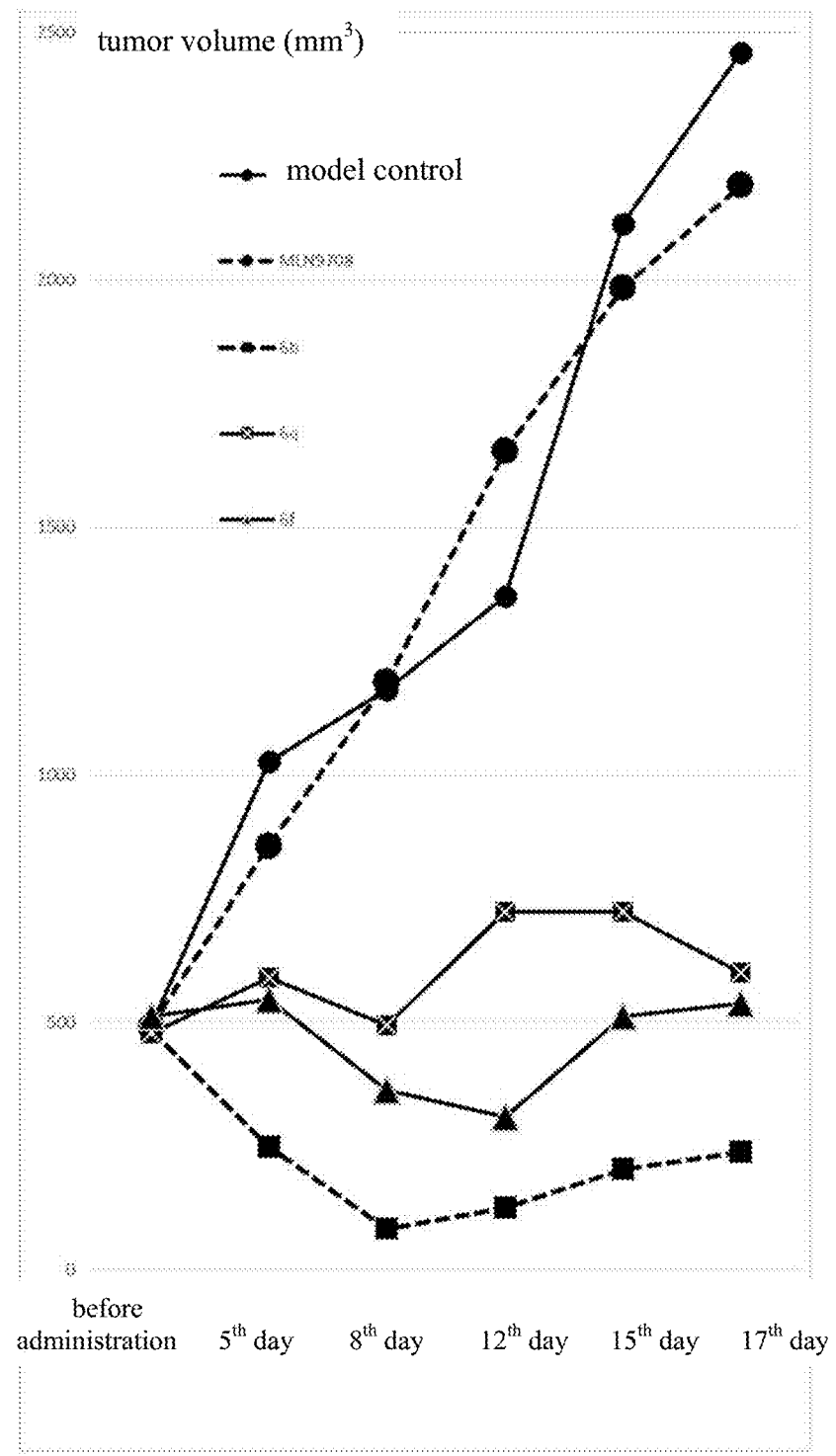
FIG. 2 is a diagram showing tumor volume of the transplantation tumor model of human multiple myeloma MM.1S in SCID mouse.

The effect of each test sample on the tumor of the transplantation tumor model of human multiple myeloma MM.1S in SCID mouse was shown in tables 5 and 6 as well as FIG. 2.

TABLE 5

Relative tumor proliferation rate T/C(%) of proteasome inhibitor against transplantation tumor model of human multiple myeloma MM.1S in SCID mouse (T/C(%) = $T_{RTV}/C_{RTV}$, $T_{RTV}$ is average relative tumor volume of the administration group, $C_{RTV}$ is the average relative tumor volume of the model control group in the same period)

| group | day 5 T/C(%) | day 8 T/C(%) | day 12 T/C(%) | day 15 T/C(%) | day 17 T/C(%) |
|---|---|---|---|---|---|
| MLN9708 | 90.08 | 112.42 | 137.07 | 97.25 | 84.29 |
| 6b | 18▲▲ | 5.86▲▲ | 9.04▲▲ | 10.59▲▲ | 9.06▲▲ |
| 6f | 65.79▲● | 43.49▲▲● | 31.17▲▲ | 30.15▲▲ | 22.86▲▲ |
| 6q | 61.25▲●● | 47.34▲▲●● | 67.42▲▲▲● | 45.35▲▲ | 29.20▲▲ |

Note:
▲$p < 0.05$ when compared with the RTV original data of MLN9708 group in the same period,
▲▲$p < 0.01$
●$p < 0.05$ when compared with the RTV original data of 6b group in the same period,
●●$p < 0.01$;
RTV original data refers to the RTV value calculated by the measured value of tumor tissue volume of each experimental animal.

TABLE 6

Tumor weight ($\bar{X} \pm SD$, g) and tumor inhibition rate of proteasome inhibitor against the transplantation tumor model of human multiple myeloma MM.1S in SCID mouse

| group | tumor weight (g) | tumor inhibition rate (%) |
|---|---|---|
| model | 2.939 ± 0.754 | — |
| MLN9708 | 2.953 ± 0.668 | −0.48 |
| 6b | 0.360 ± 0.415★★▲▲ | 87.75 |
| 6f | 0.741 ± 0.917★★▲▲ | 74.82 |
| 6q | 0.945 ± 0.603★★▲▲● | 67.85 |

Note:
★when compared with model group, p < 0.05;
★★when compared with model group, p < 0.01
▲when compared with MLN9708 group, p < 0.05,
▲▲when compared with MLN9708 group, p < 0.01;
●when compared with 6b group, p < 0.05,
●●when compared with 6b group, p < 0.01.

The above experimental results show that compound 6b can significantly inhibit tumor growth of transplantation tumor of human multiple myeloma MM.1S in SCID mouse at a low dose of 0.00554 mmol/kg; MLN9708 has no effect on inhibiting tumor growth at this dose. Compound 6b has a significantly stronger inhibitory effect on tumor growth than MLN9708(p<0.01), and the difference is statistically significant.

At a low dose of 0.00554 mmol/kg, compounds 6f and 6q can also significantly inhibit tumor growth, but the inhibitory effect is weaker than that of compound 6b.

At the same time, in terms of the onset time of tumor growth by drugs inhibition, early and rapid inhibition of tumor growth can effectively slow down the various damages of tumor tissues to the normal body and help improving survival rate. Experimental data show that on the 5th day of administration, the relative tumor proliferation rate of the 6b group was 18%, while the relative tumor proliferation rates of the 6f group and the 6q group were above 60%; on the 12th day, the relative tumor proliferation rates of the 6b group was only 9.04%, the relative tumor proliferation rates of the 6f group was 31.17%, and the relative tumor proliferation rates of the 6q group was 67.42%. Experimental data show that compound 6b has the fastest effect on tumor growth and has the strongest inhibitory activity; compound 6f has a longer onset time to control tumor growth than that of the compound 6b, and its inhibitory activity is weaker than that the compound of 6b. Although the relative tumor proliferation rate of the 6q group decreased to 29.00% on the last 17th day, the effective time of controlling tumor growth was longer than the 6f group and significantly longer than the 6b group.

In addition, according to the evaluation standard of T/C %≤40% (after statistics procession, p<0.05 is considered significant) in "Technical Guidelines for Non-clinical Research of Cytotoxic Antitumor Drugs" issued by State Food and Drug Administration in China, the time for compound 6b to reach this standard was on the 5th day of the experiment, which is earlier than the 12th day of compound 6f (the difference is significant), and it is also significantly earlier than the 17th day of compound 6q (the difference is significant).

On the other hand, according to the diagram showing tumor volume of the transplantation tumor model of human multiple myeloma MM.1S in SCID mouse shown in FIG. 2, the area under the curve of tumor volume vs. time curve of compounds 6b, 6f and 6q is ranked in an ascending sequence. The sequence is compound 6b<compound 6f<compound 6q. The area under the curve reflects the size of the tumor during the entire experiment.

In view of the above, the inhibitory effect sequence of each test sample on transplantation tumor growth of human multiple myeloma MM.1S in SCID mouse from strong to weak is as follows: 6b>6f>6q>MLN9708.

The invention claimed is:
1. A compound or stereoisomers, enantiomers, tautomers or mixture thereof, or pharmaceutically acceptable salts, solvates, prodrugs or boric anhydride thereof, wherein the compound is:

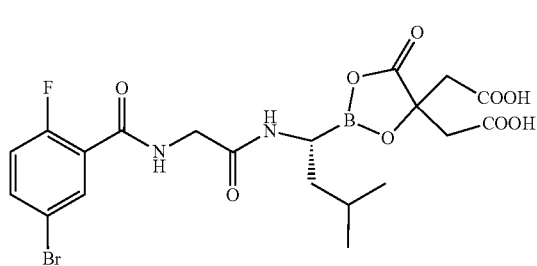

6b

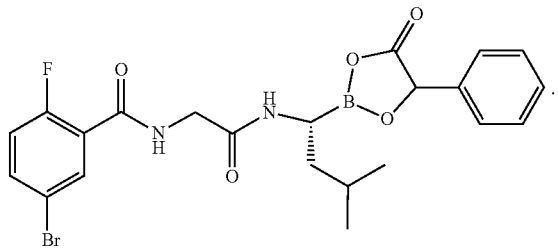

or

6f

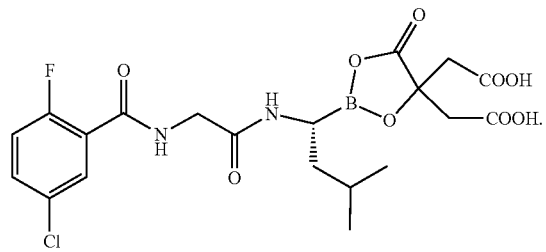

6q

2. A pharmaceutical preparation, comprising the compound or stereoisomers, enantiomer or tautomers or mixtures thereof, or pharmaceutically acceptable salts, solvates or prodrugs thereof of claim 1, and a pharmaceutically acceptable excipient.

3. A pharmaceutical composition, comprising the compound or stereoisomers, enantiomer or tautomers or mixtures thereof, or pharmaceutically acceptable salts, solvates or prodrugs thereof of claim 1, and one or more other drugs for preventing or treating tumors.

4. A method for preventing and/or treating tumors comprising administering the compound or stereoisomers, enantiomer or tautomers or mixtures thereof, or pharmaceutically acceptable salts, solvates or prodrugs thereof of claim 1 to a subject in need thereof, wherein the tumors preferably are selected from plasmacytoma, mantle cell tumor, multiple myeloma, melanoma, breast cancer, liver cancer, cervical cancer, lung cancer, lymphoma, leukemia, ovarian cancer, renal cancer, gastric cancer, nasopharyngeal cancer, thyroid cancer, pancreatic cancer, prostate cancer, adenocarcinoma, mouth cancer, esophageal cancer, squamous cell cancer and colon cancer.

5. A method for inhibiting proteasome, comprising administering the compound or stereoisomers, enantiomer or tautomers or mixtures thereof, or pharmaceutically acceptable salts, solvates or prodrugs thereof of claim 1 to a subject in need thereof.

6. A compound or stereoisomers, enantiomers, tautomers or mixture thereof, or pharmaceutically acceptable salts, solvates, prodrugs or boric anhydride thereof, wherein the compound is:

7. A pharmaceutical preparation, comprising the compound or stereoisomers, enantiomer or tautomers or mixtures thereof, or pharmaceutically acceptable salts, solvates or prodrugs thereof of claim 6, and a pharmaceutically acceptable excipient.

8. A pharmaceutical composition, comprising the compound or stereoisomers, enantiomer or tautomers or mixtures thereof, or pharmaceutically acceptable salts, solvates or prodrugs thereof of claim 6, and one or more other drugs for preventing or treating tumors.

9. A method for preventing and/or treating tumors comprising administering the compound or stereoisomers, enantiomer or tautomers or mixtures thereof, or pharmaceutically acceptable salts, solvates or prodrugs thereof of claim 6 to a subject in need thereof, wherein the tumors preferably are selected from plasmacytoma, mantle cell tumor, multiple myeloma, melanoma, breast cancer, liver cancer, cervical cancer, lung cancer, lymphoma, leukemia, ovarian cancer, renal cancer, gastric cancer, nasopharyngeal cancer, thyroid cancer, pancreatic cancer, prostate cancer, adenocarcinoma, mouth cancer, esophageal cancer, squamous cell cancer and colon cancer.

10. A method for inhibiting proteasome, comprising administering the compound or stereoisomers, enantiomer or tautomers or mixtures thereof, or pharmaceutically acceptable salts, solvates or prodrugs thereof of claim 6 to a subject in need thereof.

\* \* \* \* \*